(12) United States Patent
Chen et al.

(10) Patent No.: US 9,469,854 B2
(45) Date of Patent: Oct. 18, 2016

(54) PHARMACEUTICAL COMPOSITION FOR TREATING LIVER DISEASES

(71) Applicant: Academia Sinica, Taipei (TW)

(72) Inventors: Shui-Tein Chen, Taipei (TW); Ting-Fang Lo, Taipei (TW); Wei-Chung Tsai, Taipei (TW)

(73) Assignee: ACADEMIA SINICA, Taipei (TW)

( * ) Notice: Subject to any disclaimer, the term of this patent is extended or adjusted under 35 U.S.C. 154(b) by 0 days.

(21) Appl. No.: 14/873,275

(22) Filed: Oct. 2, 2015

(65) Prior Publication Data

US 2016/0076039 A1    Mar. 17, 2016

Related U.S. Application Data

(62) Division of application No. 14/496,280, filed on Sep. 25, 2014, now abandoned.

(30) Foreign Application Priority Data

Feb. 12, 2014 (TW) .............................. 103104537 A

(51) Int. Cl.
*A61K 48/00* (2006.01)
*C07H 21/04* (2006.01)
*C07H 21/02* (2006.01)
*C12N 15/113* (2010.01)
*A61K 31/4375* (2006.01)
*A61K 31/7105* (2006.01)

(52) U.S. Cl.
CPC ....... *C12N 15/1137* (2013.01); *A61K 31/4375* (2013.01); *A61K 31/7105* (2013.01); *C12N 15/113* (2013.01); *C12N 2310/141* (2013.01); *C12N 2320/30* (2013.01); *C12N 2320/32* (2013.01)

(58) Field of Classification Search
CPC ............................ C12N 15/113; A61K 48/00
See application file for complete search history.

(56) References Cited

U.S. PATENT DOCUMENTS

2013/0225652 A1    8/2013    Chorn et al.

*Primary Examiner* — Amy Bowman
(74) *Attorney, Agent, or Firm* — Bacon & Thomas, PLLC

(57) ABSTRACT

The present invention relates to a pharmaceutical composition for treating liver diseases, comprising a miRNA mimic containing a single strand RNA molecule of hsa-miR-21-3p (SEQ ID No: 35). The miRNA mimic of the present invention can be used to treat liver diseases through regulating the expression of methionine adenosyltransferase 2A and 2B (MAT2A and MAT2B), acetyl-CoA carboxylase 1 and 2 (ACACA and ACACB), diglyceride acyltransferase 2 (DGAT2), and so on. In addition, the present invention also relates to a method for reducing the expression of the above-mentioned enzymes.

12 Claims, 24 Drawing Sheets

C

D

PHARMACEUTICAL COMPOSITION FOR TREATING LIVER DISEASES

CROSS-REFERENCE TO RELATED APPLICATIONS

This application is a Divisional of U.S. application Ser. No. 14/496,280, filed on Sep. 25, 2014, which claims priority under 35 U.S.C. §119(a) on Patent Application No. 103104537, filed in Taiwan on Feb. 12, 2014, the contents of each are hereby expressly incorporated by reference into the present application.

BACKGROUND OF THE INVENTION

1. Field of the Invention

The present invention relates to a pharmaceutical composition for treating liver diseases, comprising a miRNA mimic containing a single strand RNA molecule of hsa-miR-21-3p (SEQ ID No: 35). In addition, the present invention also relates to a method for treating liver diseases and reducing the expression of specific enzymes.

2. Description of the Related Art

Nonalchoholic fatty liver disease (NAFLD) is rapidly becoming one of the most common liver disease because of growing prevalence of overweight and obesity. Generally, NAFLD is defined by fat accumulation, mainly triglycerides, in hepatocytes exceeding 5% of its weight. In the progress of NAFLD, intrahepatic lipid accumulation and growth of lipid droplets result in different degrees of inflammation, thereby resulting in liver fibrosis. As the clinical pathologic spectrum, liver fibrosis may progress advanced cirrhosis, hepatocellular carcinoma, hepatic decompensation, and have increased all-cause mortality. However, there is no standard drug treatment or specific therapy to reverse fatty liver disease. Nowadays, researchers are going to uncover what processes may trigger fat build-up in the liver and how to prevent and treat the fatty liver disease.

Methionine adenosyltransferase (MAT) is the cellular enzyme that catalyzes the synthesis of S-adenosyl methionine (SAM), the principal biological methyl donor and a key regulator of hepatocyte proliferation, death and differentiation[1,2]. Two genes, MAT1A and MAT2A, encode 2 distinct catalytic MAT isoforms. A third gene, MAT2B, encodes a MAT2A regulatory subunit. MAT1A is specifically expressed in the adult liver, whereas MAT2A is widely distributed[3-5]. Because MAT isoforms differ in catalytic kinetics and regulatory properties, MAT1A-expressing cells have considerably higher SAM levels than do MAT2A-expressing cells[6,7]. In hepatocellular carcinoma (HCC), the down-regulation of MAT1A and the up-regulation of MAT2A occur, which is known as the MAT1A:MAT2A switch[8-11]. The switch accompanied with up-regulation of MAT2B results in lower SAM contents, which provide a growth advantage to hepatoma cells[2,4,6,12,13]. SAM can selectively induce pro-apoptotic Bcl-Xs in hepatoma cells, but not in normal hepatocytes, through alternative splicing[14]. In addition, increased MAT2B expression in HCC also results in decreased SAM levels and facilitates cancer cell growth[15]. Because MAT2A and MAT2B play crucial role in facilitating the growth of hepatoma cells, they are valid targets for antineoplastic therapy. Recent studies have shown that silencing MAT2A and MAT2B by using small interfering RNA substantially suppress growth and induce apoptosis in hepatoma cells[16-19].

Acetyl-CoA-carboxylase, which catalyses the carboxylation of acetyl-CoA to form malonyl-CoA, exists in 2 isoforms (alpha and beta) that are separately encoded by ACACA and ACACB in mammals. ACACA, a cytosolic enzyme, is the first committed step of fatty acid synthesis in lipogenic tissue[19]. Carnitine-palmitoyl-CoA transferase I (CPT1), a rate-limiting enzyme that shuttles long-chain fatty acyl-CoAs into the mitochondria for oxidation, is rapidly inhibited by the ACACB-produced malonyl-CoA[20,21]. Diglyceride acyltransferase (DGAT), the terminal and the only committed enzyme in the biosynthesis of triacylglycerol, plays a key role in hepatic lipid droplet accumulation[22,23]. There are 2 forms of diglyceride acyltransferase which are separately encoded by DGAT1 and DGAT2. Recent studies have shown that fatty liver disease can be ameliorated or reversed by reducing the expression of ACACA, ACACB, or DGAT2, indicating that pharmacologically inhibiting these genes could be a suitable approach to treating of NAFLD[24,25].

Berberine is an isoquinoline alkaloid isolated from various medicinal herbs such as *Coptis chinensis*, and it has a wide range of pharmacological effects including anti-cancer, anti-microbial, anti-inflammatory, and anti-diabetic effects[28-29]. Recent studies have focused on its anti-tumor effects, including anti-proliferation, anti-invasion and apoptosis induction in broad tumor cell types[29-38]. In HCC, berberine has been reported to inhibit cell growth and survival through cell cycle arrest and the activation of autophagic and mitochondrial apoptotic cell death[39-41]. In addition, some reports have shown that berberine has hypoglycemic, hypolipidemic and LDL-lowing effects, and animal studies have proved that berberine reduces the liver fat content in vivo.

MicroRNAs (miRNAs) are small non-coding RNA molecules composed of 21-23 nucleotides that play a critical role in a wide variety of biological processes, including development, proliferation, and death[42,43]. The deregulated expression of miRNAs is observed in numerous human cancer types, and they can act as tumor suppressors or oncogenes in the tumorigenic process[44,45]. Mature miRNAs typically direct their posttranscriptional repression by pairing the seed region of the miRNA to 3' UTRs, the non-coding sequence at the 3' end of target genes, leading to mRNA destabilization and translational silencing[46,47]. The seed region of miRNAs locates at the 5' end, from the second to eighth nucleotide. When the seed region pairs with the 3' UTR of the target gene, it silences the gene. It is not necessary for the miRNA being completely complementary to the 3' UTR of the target gene. The processing of the precursor miRNA (pre-miRNAs) hairpin generates an miRNA duplex consisting of a guide strand and a passenger strand (also termed as miRNA and miRNA*). By convention, a guide strand is selectively loaded onto an Argonaute (AGO) protein to form an miRNA-induced silencing complex (miRISC), and the passenger strand is believed to be preferentially degraded because of its lower steady-state level[48]. However, current research shows that numerous miRNA* species accumulate to substantial levels, and endogenous miRNA genes do not universally exclude miRNA* species from functional miRISC complexes, which suggests that miRNA* species should be considered[49-54].

SUMMARY OF THE INVENTION

In this invention, we used miRNA microarray and found that the expression level of hsa-miR-21-3p increased after berberine treatment in human hepatoma cell line (HepG2) and primary human hepatocytes (PHHs). With whole-genome microarray, bioinformatics software and a series of experiments, we have found that the miR-21-3p (one of the mature miRNAs of MIR21 gene) mimic reduces the expression of MAT2A, MAT2B and EEF2K in hepatocellular carcinoma cells, increases intracellular SAM concentration, inhibits cancer cell growth and induces apoptosis in hepatoma. In addition, the miR-21-3p mimic also decrease the lipid droplet contents in primary human hepatocytes, inhibits the expression of ACACA, ACACB and DGAT2, and reduces the expression of lipid biosynthesis-related genes, including HLCS, MTOR, RPTOR, in primary human hepatocytes, thereby decreasing lipid biosynthesis in liver, promoting lipid oxidation and ameliorates fatty liver diseases.

One object of the present invention is to provide a pharmaceutical composition comprising a microRNA mimic which inhibits cancer cell growth and induces apoptosis in hepatoma, decreases lipid biosynthesis, promotes lipid oxidation and ameliorates fatty liver diseases.

Another object of the present invention is to provide a method for decreasing the expression of methionine adenosyltransferase 2A and 2B (MAT2A and MAT2B), in which these enzymes relate to inhibition of cancer cell growth and induction of apoptosis in hepatoma, and can be applied for the treatment for liver cancers.

Yet another object of the present invention is to provide a method for decreasing the expression of acetyl-CoA carboxylase 1 and 2 (ACACA and ACACB) and diglyceride acyltransferase 2 (DGAT2), in which these enzymes relate to reduction of lipid metabolism and triglyceride biosynthesis, and can be applied for the treatment of fatty liver diseases.

The present invention provides a pharmaceutical composition for treating liver diseases, comprising a microRNA mimic containing a single strand RNA molecule of hsa-miR-21-3p (SEQ ID No: 35).

In the preferred embodiments of the present invention, said pharmaceutical composition comprise a microRNA mimic which is a single strand RNA molecule of hsa-miR-21-3p (SEQ ID No: 35).

In the preferred embodiments of the present invention, said microRNA mimic is chemically modified for not being degraded by RNase; more preferably, said microRNA mimic is chemically modified to form a O2', C4'-methylene bridge between the second O molecule and fourth C molecule of riboses, which is a stable locked nucleic acid (LNA) form. Such a chemically modified nucleic acid molecule can be directly administered to patients without any drug carrier.

In the preferred embodiments of the present invention, said microRNA mimic is delivered into target cells by a general delivery method used for RNA drugs, including delivering said microRNA mimic into target cells by transfection and/or conjugate delivery. Regarding with transfection, said microRNA mimic is delivered into target cells by using liposome, exosome, nanoparticle, virus, and the like; in which said nanoparticle comprises lipid nanoparticle (LNP) or polymer nanoparticle such like chitosan. Regarding with conjugate delivery, said microRNA mimic is delivered into target cells after binding with an aptamer or cholesterol. For example, the microRNA mimic of the present invention is directly modified to bind with an aptamer; therefore, when it is administered into the body, the aptamer will bind the target cells and delivers the microRNA mimic of the present invention into the target cells. Alternatively, the microRNA mimic of the present invention is covalently binding with cholesterol; therefore, when the conjugate is administered into the body, it will be taken by hepatic cells having low-density lipoprotein (LDL) receptors on their surfaces. Moreover, the combination of conjugate delivery and transfection also can be used. For example, the microRNA mimic of the present invention can be conjugated with an aptamer to form a conjugate, and then the conjugate is transfected into the target cells by a transfecting agent (such like liposome).

In the preferred embodiments of the present invention, said pharmaceutical composition can be administered orally or parenterally; more preferably, it is administered by injection; even more preferably, it is administered by intravenous injection.

In the preferred embodiments of the present invention, said liver diseases comprise liver cancers and fatty liver diseases.

In the preferred embodiments of the present invention, said pharmaceutical composition treats liver cancers though decreasing the expression of methionine adenosyltransferase 2A and 2B (MAT2A and MAT2B).

In the preferred embodiments of the present invention, said pharmaceutical composition treats fatty liver diseases though decreasing the expression of acetyl-CoA carboxylase 1 and 2 (ACACA and ACACB) and diglyceride acyltransferase 2 (DGAT2).

The present invention also provides a use of a microRNA mimic containing a single strand RNA molecule of hsa-miR-21-3p (SEQ ID No: 35) for preparing a drug for liver cancers.

The present invention also provides a use of a microRNA mimic containing a single strand RNA molecule of hsa-miR-21-3p (SEQ ID No: 35) for preparing a drug for fatty liver diseases.

The present invention also provides a method for decreasing the expression of acetyl-CoA carboxylase 1 and 2 (ACACA and ACACB) and diglyceride acyltransferase 2 (DGAT2) by administering berberine or a microRNA mimic containing a single strand RNA molecule of hsa-miR-21-3p (SEQ ID No: 35).

In the preferred embodiments of the present invention, the method for decreasing the expression of ACACA, ACACB and DGAT2 comprises administering berberine or a microRNA mimic which is a single strand RNA molecule of hsa-miR-21-3p (SEQ ID No: 35).

Yet, the present invention provides a method for decreasing the expression of methionine adenosyltransferase 2A and 2B (MAT2A and MAT2B) by administering berberine or a microRNA mimic containing a single strand RNA molecule of hsa-miR-21-3p (SEQ ID No: 35).

In the preferred embodiments of the present invention, the method for decreasing the expression of MAT2A and MAT2B comprises administering berberine or a microRNA mimic which is a single strand RNA molecule of hsa-miR-21-3p (SEQ ID No: 35).

The present invention provides a pharmaceutical composition comprising a microRNA mimic which is a single strand RNA molecule of hsa-miR-21-3p (SEQ ID No: 35), wherein the microRNA mimic of hsa-miR-21-3p improves liver function through many working mechanisms and induces cancer cell apoptosis. Thus, it is potential for treating liver diseases.

DETAILED DESCRIPTION OF THE PREFERRED EMBODIMENTS

Figure 1A:
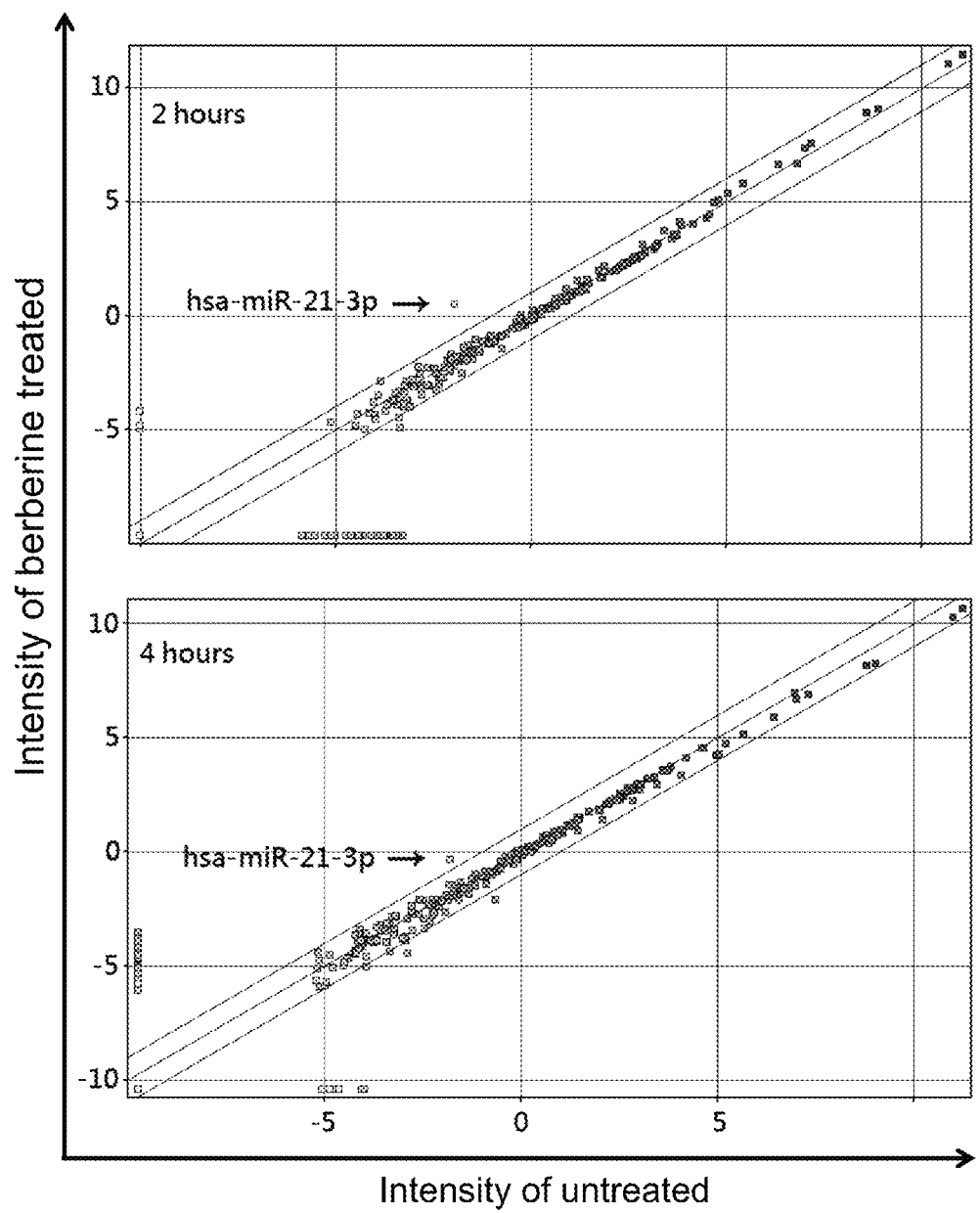
FIG. 1A represents the scatter plot showing the comparison of the miRNA expression profiles between berberine-treated and untreated HepG2 cells. The arrow indicates that hsa-miR-21-3p is the only miRNA that increases in HepG2 cell line after 40 μM berberine treatment for 2 h and 4 h. The diagonal lines represent that the induced fold changes are between the boundary values of 2 and 0.5.

In the present invention, the data obtained by miRNA microarray analysis have proved that the expression level of hsa-miR-21-3p increased after berberine treatment in human hepatoma cell line (HepG2). We integrated the gene expression profiles of HepG2 cells after berberine treatment and the gene list that we generated from sequence-based miRNA target prediction software to obtain the putative targets of miR-21-3p, i.e. MAT2A, DIDO1, EEF2K, NBPF8 and TMEM137. The following experiments prove that miR-21-3p inhibits the expression of MAT2A directly, and it also targets to the 3' UTR of MAT2B to inhibit the expression of MAT2B. In addition, the over-expression of miR-21-3p increase intracellular SAM contents, which has been proven to reduce the cell growth of hepatoma. We have also found that miR-21-3p reduces the expression of EEF2K. EEF2K has been reported as a putative target for anti-cancer therapy because it promotes the growth of tumor and resists to cell apoptosis[55]. Therefore, miR-21-3p over-expression will inhibit the cell growth of HepG2 and induces apoptosis. The results show that miR-21-3p works as a tumor suppressor and potential for treating HCC.

Cell Culture and Treatment

The human HepG2 cells and HEK 293T cells used in the following examples were originally obtained from the American Tissue Culture Collection (ATCC, USA). The human HCC HepG2 cell line was cultured in Minimum Essential Medium Eagle (Sigma) supplemented with 10% fetal bovine serum (FBS) (Invitrogen), 2.2 g/L of sodium bicarbonate (Sigma), 0.1 mM of non-essential amino acids (Caisson), 1 mM of sodium pyruvate (Invitrogen), and 10 of ml/L penicillin-streptomycin-amphotericin solution (Biological Industries). Human HEK-293T cells were maintained in high-glucose Dulbecco's modified eagle medium (Invitrogen) supplemented with 10% FBS and 3.7 g/L of sodium bicarbonate (Sigma). Both cell lines were cultured at 37° C. and 5% $CO_2$.

The primary human hepatocytes from Caucasian donors were purchased from Invitrogen and cultured following the manufacturer's instructions. The hepatocytes were thawed and transferred into cryopreserved hepatocytes recovery medium (CM7000, Invitrogen), centrifuging at room temperature, 100×g for 10 min. Then, the hepatocytes were diluted to seeding density with plating medium (CM3000, Invitrogen) and added into collagen I-coated plates (Invitrogen). These plates were incubated at 37° C. for 4-6 hours under 5% $CO_2$ for forming a monolayer. Then, plating medium was replaced by overlay incubation medium (CM4000 and 0.35 mg/mL Geltrex™ Matrix, Invitrogen), and the incubation medium was replaced daily. In the following examples, hepatocytes form 3 to 4 donors were used for experiments.

A 50 mM stock solution of berberine chloride (Sigma-Aldrich) was prepared in dimethyl sulfoxide (DMSO). Cells were treated with 40 μM of berberine chloride or 0.08% DMSO as the control. For induction of lipid droplets formation in cultured cells, 200 μM of oleic acid (Sigma-Aldrich) was added into the culture medium for 24 h.

RNA Isolation

Total RNA was extracted using a TRIZOL reagent (Invitrogen) according to the manufacturer's protocol. The total RNA quantity was measured using a NanoDrop ND-1000 spectrophotometer (Nanodrop Technologies). The total RNA quality and integrity were assayed using an Agilent 2100 bioanalyzer with an RNA 6000 nano kit (Agilent Technologies).

Microarray

The miRNA profiling was performed using an Agilent human miRNA Microarray R14 V2 containing 866 human miRNAs. The labeling and hybridization of total RNA were performed by following the standard protocol of Agilent's miRNA microarray system of SurePrint G3 human GE 8×60K microarrays (Agilent Technologies). Microarrays were scanned following the Agilent microarray scanner protocol, and image analysis and quantification were performed using the Agilent Feature Extraction software (Agilent Technologies). GeneSpring Gx software (Agilent Technologies) was used to identify miRNAs that were differentially expressed (fold-change >2) between the berberine-treated and untreated samples. The gene expression microarray was performed using a HumanHT-12 v4 Expression BeadChip (Illumina). The labeled cRNA was generated from an RT-IVT Kit (Ambion) and a TotalPrep RNA amplification kit (Illumina). The labeled cRNA was then hybridized to microarrays following the manufacturer's protocol. GenomeStudio software (Illumina) was used to identify miRNAs that were differentially expressed (fold-change >1.5 and P<0.05) between the berberine-treated and untreated samples. All microarray data were deposited in the NCBI GEO database (GSE47822 and GSE53416).

Quantitative Real-Time RT-PCR (qRT-PCR)

(1) MicroRNA Assays

Total RNAs (1 ng) were reverse-transcribed into cDNA by using TaqMan Small RNA Assays kits with hsa-miR-21-3p-, hsa-miR-21-5p- or RUN6B-specific RT primers (Invitrogen). The microRNA expression levels were normalized to RNU6B levels.

(2) Gene Expression Assays

Total RNAs (1 μg) were reverse-transcribed into cDNA by using M-MuLV Reverse Transcriptase (Thermo) and Oligo(dT)12-18 primers (Invitrogen) according to the manufacturer's protocol. The cDNA were then used for a real-time PCR with a LightCycler 480 SYBR Green I Master (Roche) by using primers shown in the following Table 1. The gene expression levels were normalized to GAPDH levels.

TABLE 1

| primers used for gene expression detection | |
|---|---|
| MAT1A primers | 5'-GCCAAGGGCTTTGACTTC-3' (SEQ ID No: 1)<br>5'-CTGTCTCGTCGGTAGCATA-3' (SEQ ID No: 2) |
| MAT2A primers | 5'-ACAATCTACCACCTACAGCC-3' (SEQ ID No: 3)<br>5'-CCAACGAGCAGCATAAGC-3' (SEQ ID No: 4) |
| MAT2B primers | 5'-TGGTTTCAGAAGAGCAAGAC-3' (SEQ ID No: 5)<br>5'-ATTCCCAGAAGCATCCAC-3' (SEQ ID No: 6) |
| DIDO1 primers | 5'-GATGAGGAGCCTGGAGAC-3' (SEQ ID No: 7)<br>5'-AGAAATGCCCACACAATCG-3' (SEQ ID No: 8) |
| EF2K primers | 5'-GGCAAACTCCTTCCACTTCA-3' (SEQ ID No: 9)<br>5'-CATCATCCAGCCATTCCC-3' (SEQ ID No: 10) |
| NBPF8 primers | 5'-CAGGACATCGGTGGAATCA-3' (SEQ ID No: 11)<br>5'-CTTCTGTAGGGCTGGCAT-3' (SEQ ID No: 12) |
| TMEM137 primers | 5'-GAAGACTGGTTGAGTGGGAT-3' (SEQ ID No: 13)<br>5'-TGTCACAGGCAAGTTCACAT-3' (SEQ ID No: 14) |
| ACACB primers | Hs_ACACB_1_SG QuantiTect primer assay<br>QT00996352primer (Qiagen) |
| HLCS primers | 5'-AGTCAGTCAAGTTTGCGTC-3' (SEQ ID No: 15)<br>5'-GAGTCGGAGCCCACATAGA-3' (SEQ ID No: 16) |
| MTOR primers | 5'-CGTCCCTACCTTCTTCTTCC-3' (SEQ ID No: 17)<br>5'-TACCACTGAGGCTTCTGC-3' (SEQ ID No: 18) |
| RPTOR primers | 5'-ACTTCCCGCTCAGAGTTAGA-3' (SEQ ID No: 19)<br>5'-CGAGAACCTCCAGCCTTA-3' (SEQ ID No: 20) |
| ACSM2A primers | 5'-CTCCGCAACTTAGGATGGG-3' (SEQ ID No: 21)<br>5'-CTCTCTCTGTCTCTCTCTCG-3' (SEQ ID No: 22) |
| NAMPT primers | 5'-GCAAGTCTGTTGGTGCTAT-3' (SEQ ID No: 23)<br>5'-TTATCTGGGTGTGCCCTG-3' (SEQ ID No: 24) |
| IL6R primers | 5'-GTGGTAGCCGAGGAGGAA-3' (SEQ ID No: 25)<br>5'-GGTCAGAGTCACGCTGTC-3' (SEQ ID No: 26) |
| SREBF2 primers | 5'-TACCTTCCTTCTCTCCCTCG-3' (SEQ ID No: 27)<br>5'-GTGGTGCTGAATGTTGGC-3' (SEQ ID No: 28) |
| ACACA primers | 5'-TTTGTGCCACGGTTATCAT-3' (SEQ ID No: 29)<br>5'-CCAAGTAATAGCCAGACTCG-3' (SEQ ID No: 30) |
| DGAT2 primers | 5'-GAAGTTCCCAGGCATACG-3' (SEQ ID No: 31)<br>5'-GACCACGATGATGATAGCATTG-3' (SEQ ID No: 32) |
| GAPDH primers | 5'-GGTATCGTGGAAGGACTCAT-3' (SEQ ID No: 33)<br>5'-CCTTGCCCACAGCCTTG-3' (SEQ ID No: 34) |

Transfection of MicroRNA Mimics and Inhibitors

The present invention also uses miRNA mimics and inhibitors for transfection experiments. miRNA mimics are used to observe the effects induced by the miRNA, and miRNA inhibitors are used to inhibit the expression of endogenous miRNA in cells to make the expression of target gene stronger.

All of the miRNA mimics and inhibitors were purchased from Thermo Scientific Dharmacon, comprising:

| | |
|---|---|
| hsa-miR-21-3p mimic | CAACACCAGUCGAUGGGCUGU (SEQ ID No: 35) The name shown in miRNA database is hsa-miR-21-3p (No. MIMAT0004494) |
| NC mimic | UCACAACCUCCUAGAAAGAGUAGA (SEQ ID No: 36) The name shown in miRNA database is Cel-mir-67 (No. MIMAT0000039) |
| hsa-miR-21-3p inhibitor | miRIDIAN Hairpin Inhibitor hsa-miR-21-3p (purchased from Thermo Scientific Dharmacon), an RNA sequence which can bind SEQ ID No: 35 |
| NC inhibitor | miRNA Hairpin Inhibitor N-ctrl #1 (purchased from Thermo Scientific Dharmacon), an RNA sequence which can bind SEQ ID No: 36 |

The HepG2 cells were transfected at a density of $5 \times 10^4$ cells per well in a 24-well culture plates with either 50 nM of hsa-miR-21-3p (miR-21-3p mimic) or negative-control mimic (NC mimic), or with either 100 nM of hsa-miR-21-3p inhibitor (miR-21-3p inhibitor) or negative-control inhibitor (NC inhibitor) by using the DharmaFECT 4 transfection reagent (Thermo Scientific Dharmacon) according to the manufacturer's instructions. Cells were incubated for 24 h or 48 h with a microRNA mimic or inhibitor prior to RNA purification for gene expression analysis, and were incubated for 72 h for protein expression analysis.

Western Blotting

Total cell lysates were prepared using a lysis buffer (7 M of urea, 4% CHAPS, 2 M of thiourea, 40 mM of Tris, 65 mM of dithioerythritol). Protein samples were separated using 12.5% SDS-PAGE and then transferred to PVDF membranes. The following primary antibodies were used: rabbit polyclone anti-MAT1A (1:800, GeneTex), anti-MAT2A (1:1000, GeneTex), anti-MAT2B (1:1000, GeneTex), anti-ACACB (1:1000, Sigma), anti-DGAT2 (1:1000, GeneTex) and anti-GAPDH (1:3000, GeneTex) and mouse monoclone anti-ACACA (1:1000, Millipore). The goat polyclonal anti-rabbit or anti-mouse IgG antibody conjugated with HRP (1:5000, abcam) was used as the secondary antibody. The bands were imaged using the LAS-4000 mini luminescent image analyzer (Fujifilm). The quantification of western blot analysis was achieved by using Image J software. The protein expression levels were normalized to the GAPDH levels.

Construction of the Luciferase Reporter Plasmids

Full-length 3' UTRs of MAT2A and MAT2B were amplified from the genomic DNA of HepG2 cells through PCR.

TABLE 3 primers used to amplify 3' UTR sequences

| | |
|---|---|
| MAT2A 3' UTR Primers | forward primer with a SpeI restriction site 5'-ATAACTAGTGTGTTAGCCTTTTTTCCCCAG-3' (SEQ ID No: 37) reverse primer with a HindIII restriction site 5'-ATAAAGCTTGCACTTTCTGCTTAGGGCAA-3' (SEQ ID No: 38) |

TABLE 3 -continued primers used to amplify 3' UTR sequences

| | |
|---|---|
| MAT2B 3' UTR primers | forward primer with a MluI restriction site 5'-ATAACGCGTTGGCACTTTTTAAAGAACAAAGG-3' (SEQ ID No: 39) reverse primer with a HindIII restriction site 5'-ATAAAGCTTAAAAATTAAAGCAACAAAAGAACAA-3' (SEQ ID No: 40) |

The PCR products were then cloned into the pMIR-REPORT Luciferase miRNA Expression Reporter Vector (Invitrogen), and all inserted sequences in the 3' UTR constructs were checked using the ABI PRISM DNA sequencer.

Mutagenesis and Plasmid Construction

The mutagenesis of the target sequences of hsa-miR-21-3p in MAT2A and MAT2B 3' UTRs was performed using the QuikChange site-directed mutagenesis kit (Agilent) according to the manufacturer's standard protocol.

TABLE 4 primers used for sited-mutagenesis in 3' UTR sequences

For the mutagenesis of Site 1 (+180-200) in the 3' UTR of MAT2A
5'-CAGCTCTGCCCTCCCTTCTGTTGATATCAGCCAGACCCC-3'
(SEQ ID No: 41)

For the mutagenesis of Site 2 (+1267-1288) in the 3' UTR of MAT2A
5'-CACTAAATTCATTATAATGGTGAACAAGATATCTAGGGACAGA
ATAGCAAGCCCAACT-3'
(SEQ ID No: 42)

For the mutagenesis of the target site (+399-418) in the 3' UTR of MAT2B
5'-TTTGATCTGAGCTCAGGCAAAGCAAATAATGGATATCAATGAT
TTTTATACTATTTCACACAATTTAA-3'
(SEQ ID No: 43)

All mutated sequences, including Site 1, Site 2 and the double mutation of the MAT2A and the 3' UTR mutant construct of MAT2B, were checked through DNA sequencing.

Dual Luciferase Reporter Assay

The HEK-293T and HepG2 cells were seeded at a density of $5 \times 10^4$ cells per well in a 24-well culture plate the day before transfection. The HEK-293T and HepG2 cells were tri-transfected with (1) any one of the above-mentioned pMIR-REPORT-3' UTR construction (300 ng), (2) the control Renilla luciferase reporter plasmid pRL-TK from Promega (10 ng), and (3) 50 nM of hsa-miR-21-3p mimic or negative-control mimic by using the Lipofectamine 2000 transfection reagent (Invitrogen) according to the manufacturer's instructions. Luciferase assays were performed after transfection for 48 h by using the Dual Luciferase reporter assay kit (Promega) and the Paradigm detection platform (Beckman) according to the manufacturer's protocol. The firefly luciferase activity was normalized relative to the Renilla luciferase activity.

Measurement of Intracellular SAM Concentration

After transfection with 50 nM of hsa-miR-21-3p mimic or the negative-control mimic for 72 h, the HepG2 cells were trypsinized and counted. The intracellular SAM of $5 \times 10^4$ HepG2 cells pellet was resuspended in 30 mL of an extraction solution (0.2% perchloric acid plus 0.08% (v/v) 2-mercaptoethanol in ddH2O). Cells were incubated at room temperature for 1 h and vortexed every 5 min. The suspension was centrifuged at 4° C. at 10000×g for 5 min, and then the supernatant was collected. SAM levels in the supernatants were quantified using the Bridge-It SAM fluorescence assay kit (Mediomics) and detected using SpectraMax plate reader (Molecular Devices) according to the manufacturer's instructions.

Cell Proliferation Assay

The HepG2 cells were seeded at a density of $1 \times 10^4$ cells per well in a 96-well culture plate the day before transfection. After transfection with 50 nM of hsa-miR-21-3p mimic or the negative-control mimic for 24 h, the cultured media were refreshed with complete media containing the BrdU reagent, and incubated for an additional 24 hour for BrdU incorporation. The BrdU incorporation was quantified by using the BrdU cell proliferation colorimetric ELISA kit (abcam) according to the manufacturer's protocol and detected using the MRX II microplate reader (DYNEX).

Detection of Apoptosis and Intracelluar Lipid Droplet Contents by Using Flow Cytometry After transfection with 50 nM of hsa-miR-21-3p mimic or the negative-control mimic for 72 h, the HepG2 cells were trypsinized and counted. Apoptosis was detected by measuring the sub-G1 population by using flow cytometry with propidium iodide (PI) staining. In brief, the cells were fixed in 70% ethanol on ice for 15 min, and stained with the PI staining solution (20 µg/mL PI, 0.1% Triton-X 100, and 0.2 mg/mL RNase A in PBS) for 30 min at room temperature and analyzed using CyAn ADP (Beckman Coulter) flow cytometry with Summit software.

The intracellular lipid droplets were detected by measuring the geometric means of fluorescence intensity using flow cytometry with BODIPY 493/503 (Invitrogen) staining. In brief, the cells were fixed in 70% ethanol at 4° C. for 20 min, and stained with the BODIPY staining solution (10 µg/mL in 70% ethanol) (Invitrogen) for 20 min at room temperature and analyzed using CyAn ADP (Beckman Coulter) flow cytometry with Summit software.

Measurement of Intracellular Malonyl-CoA Concentration

After transfection with 50 nM of miR-21-3p mimic or the negative-control mimic for 72 h, the PHH cells and HepG2 cells were trypsinized. The intracellular malonyl-CoA concentration was measured using the malonyl-CoA ELISA Kit (MyBioSource) according to the manufacturer's instructions.

The following examples are given to illustrate the present invention, and not meant to limit the scope of the present invention. Those skilled in the art will appreciate that the present invention can be practiced by other than the disclosed embodiments. All cited reference are incorporated herein by references.

EXAMPLES

Example 1

Increased miR-21-3p Expression after Berberine Treatment in HepG2 Cell Lines

Figure 1B:
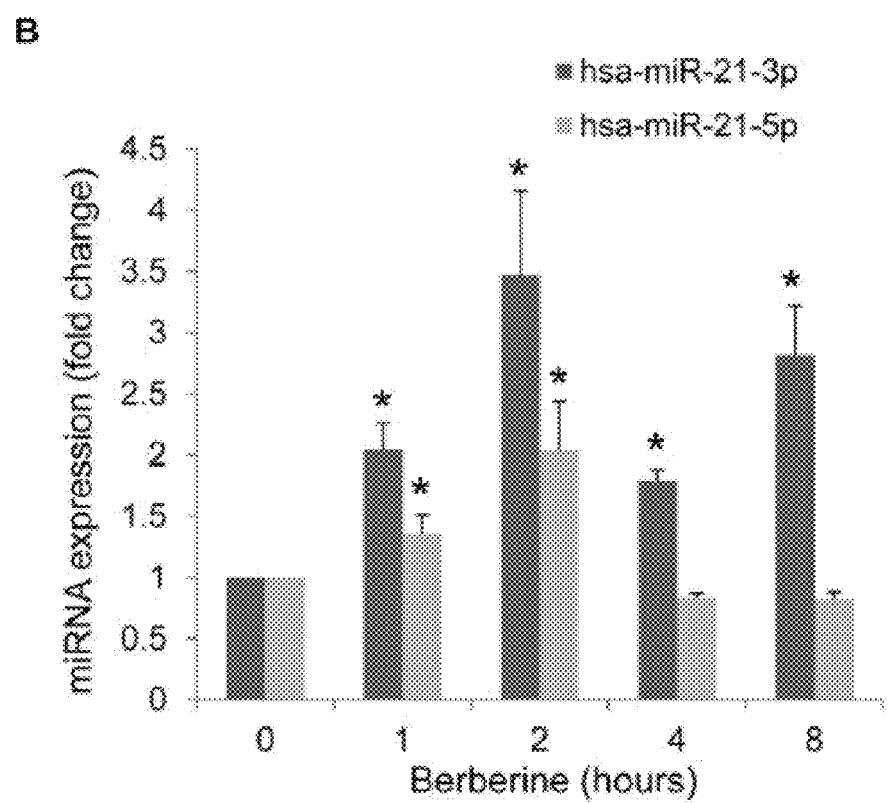
FIG. 1B represents the changes of HepG2 cells stimulated by the time course of 40 µM berberine treatment for up to 8 h compared with the untreated control. The hsa-miR-21-3p and hsa-miR-21-5p levels are measured by qRT-PCR, which are shown in folds. The data are represented as the mean±standard deviation for 3 independent experiments. The asterisk mark "*" indicates a significant difference with $P<0.05$.

Because xenobiotic drug-induced miRNAs have recently emerged as key regulators in guiding their pharmacological effects and toxicity[56,57], we examined whether miRNA expression is differentially altered by berberine treatment in HCC To identify miRNAs induced by berberine treatment, miRNA profiling was performed with an Agilent human miRNA microarray containing probes for 866 human miRNAs. Comparing the miRNA profiles of 40 µM of the berberine-treated HepG2 human hepatoma cell line to those of control cells sampled after 2 h and 4 h of treatment shows that only hsa-miR-21-3p (in which hsa represents human, miR represents mature miRNA, 21 represents the order of discovery, and 3p represents it is the 3p miRNA of the two complementary mature miRNAs, i.e. 3p and 5p, resulted from the pre-miRNA) (previously named as miR-21*) had increased in the HepG2 cell line after berberine treatment (4-fold increase) (FIG. 1A). To further assess the relevance of miR-21-3p in berberine treatment, qRT-PCR assays were used to measure the miR-21-3p expression in HepG2 stimulated by the time course of berberine treatment for up to 8 h compared with the untreated control. As shown in FIG. 1B, miR-21-3p levels started to increase substantially by 1 h (2.1-fold increase) after treatment, peaked at 2 h (3.5-fold increase), and persisted until 8 h (2.8-fold increase). In addition, miR-21-5p (the miRNA formed from the same pre-miRNA and partially complementary to 3p) (previously named as miR-21) increased 2-fold after 2 h of treatment, whereas no significant differences in miR-21-5p expression were detected at 4 h and 8 h. These results show that berberine treatment could significantly up-regulate miR-21-3p expression.

Example 2

Multiple Species Alignments Show that miR-21-3p is Conserved Over the Mammalian Evolution The final fate of the miRNA* strand, either expressed abundantly as a potential functional guide miRNA or degraded to a passenger strand, may be destined across evolution[54]. Well-conserved miRNA* strands in seed sequences may afford potential opportunities for contributing to the regulation network[52].

Figure 2:
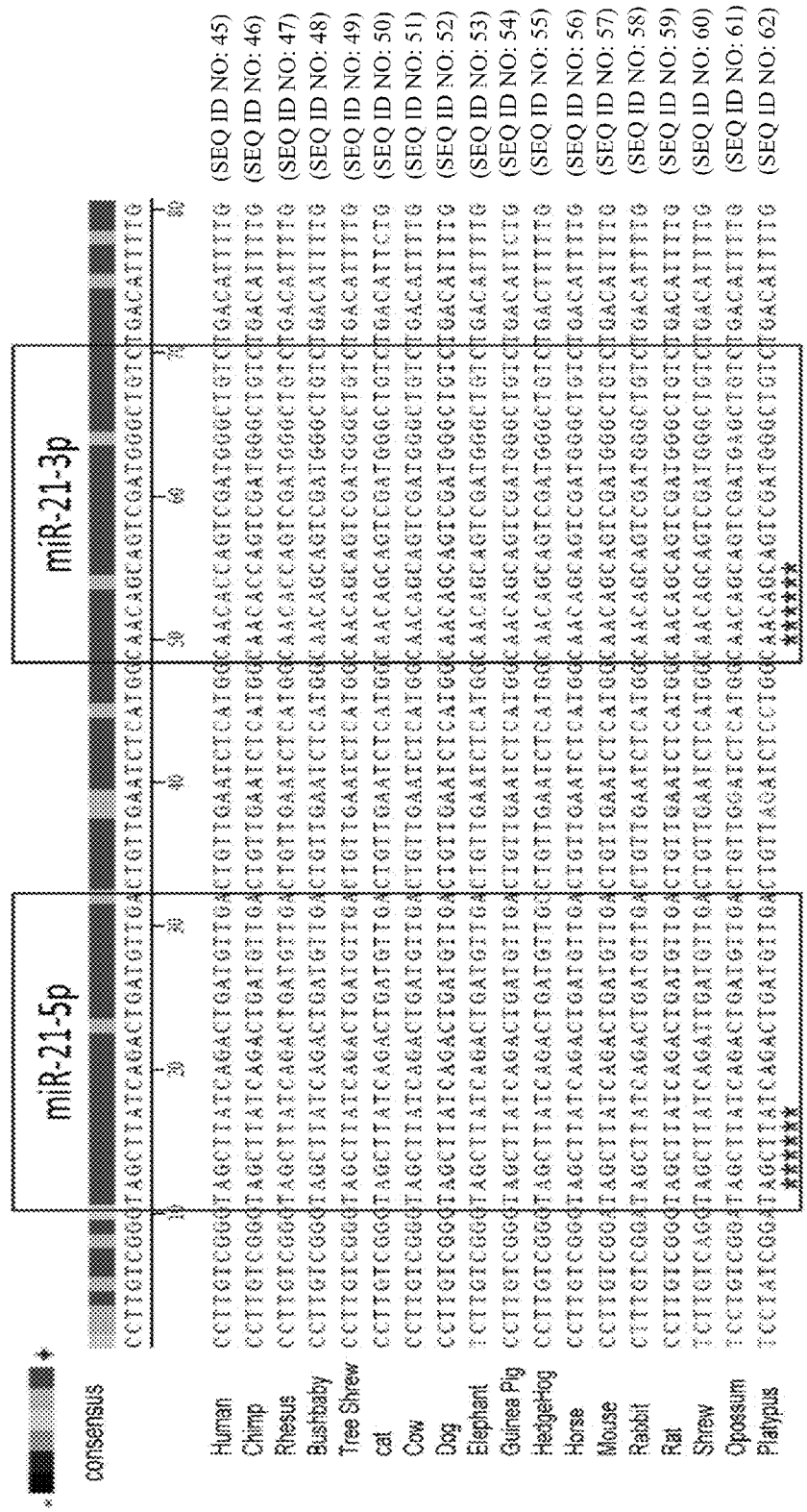
FIG. 2 represents the comparison of the MIR21 gene sequences of 18 mammalian species (SEQ ID No: 45 to SEQ ID No: 62), which shows that the MIR21 gene is conserved over the mammalian evolution. The asterisk mark indicates the seed region of miRNAs.

As shown in FIG. 2, we analyzed the MIR21 gene with respect to the 18-way alignments of mammalian genomes from the UCSC genome browser, and found that miR-21-3p shows conservation over the mammalian evolution. Based on the results of sequence comparisons, we found that human MIR21 has the closest evolutionary relationships with chimpanzee and rhesus macaque MIR21. Furthermore, one nucleotide substitution is in the seed region of miR-21-3p from humans, chimpanzees, and rhesus macaques compared to the remaining 15 mammals. This one nucleotide substitution, MIR21 (+54 G to C), replaces the fifth nucleotide of the conserved seed region of miR-21-3p, which may alter the regulatory role of miR-21-3p in humans, chimpanzees and rhesus macaques from remaining 15 mammals.

From FIG. 2, it is found that the seed region sequence of hsa-miR-21-3p, the microRNA mimic of the present invention, is ACCACC (SEQ ID No. 44).

Example 3

MicroRNA-21-3p Target Prediction and Validation

Figure 3A:
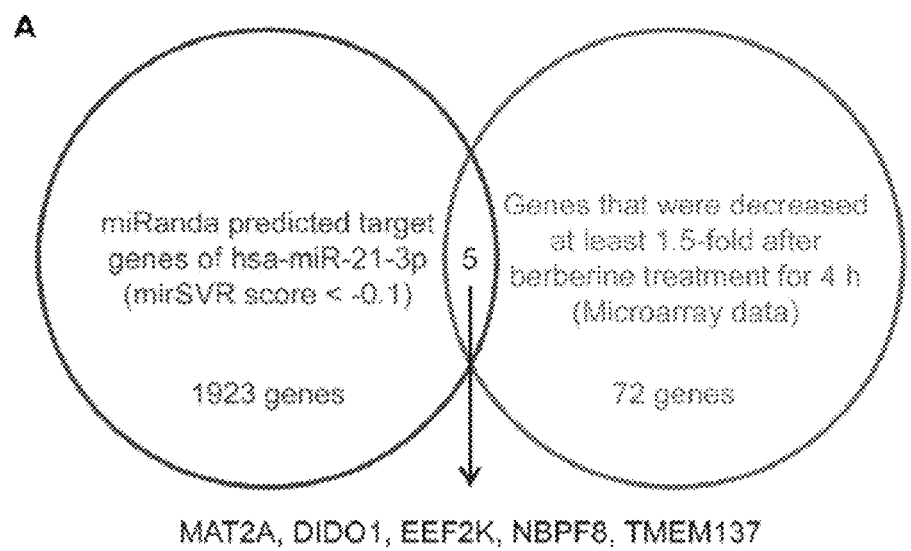
FIG. 3A represents that the target genes of miR-21-3p predicted using the miRanda algorithm and an mirSVR score threshold of <−0.1 are overlapped with the genes negatively regulated after berberine treatment in HepG2 cells according to the microarray data, in which 5 genes targets are present in both groups: MAT2A, DIDO1, EEF2K, NBPF8 and TMEM137.
Figure 3B:
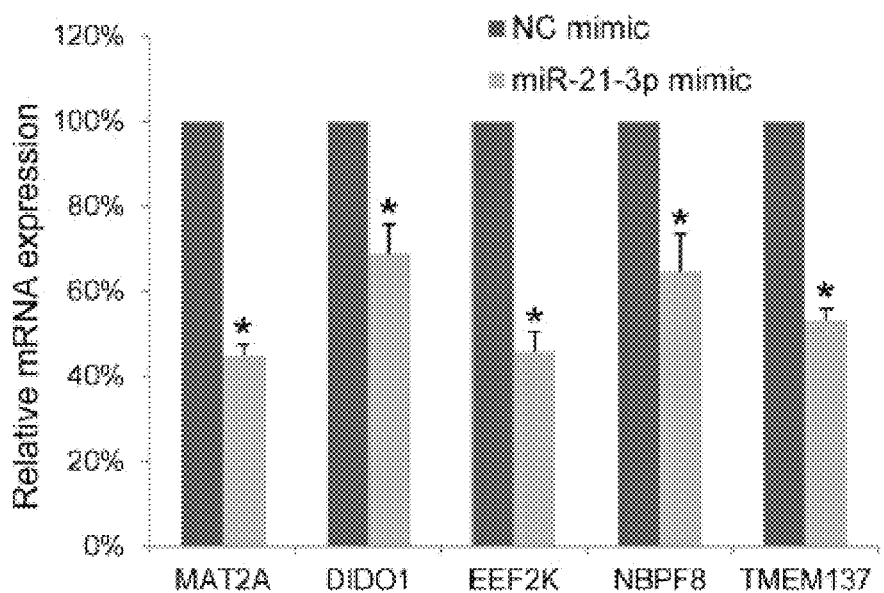
FIG. 3B represents the mRNA expression levels of MAT2A, DIDO1, EEF2K, NBPF8, and TMEM137 in HepG2 cells after transfection of 50 nM of miR-21-3p mimic or negative-control (NC) mimic. The mRNA expression is measured using qRT-PCR. The data are represented as the mean±standard deviation for 3 independent experiments. The asterisk mark "*" indicates a significant difference with $P<0.05$.
Figure 3C:
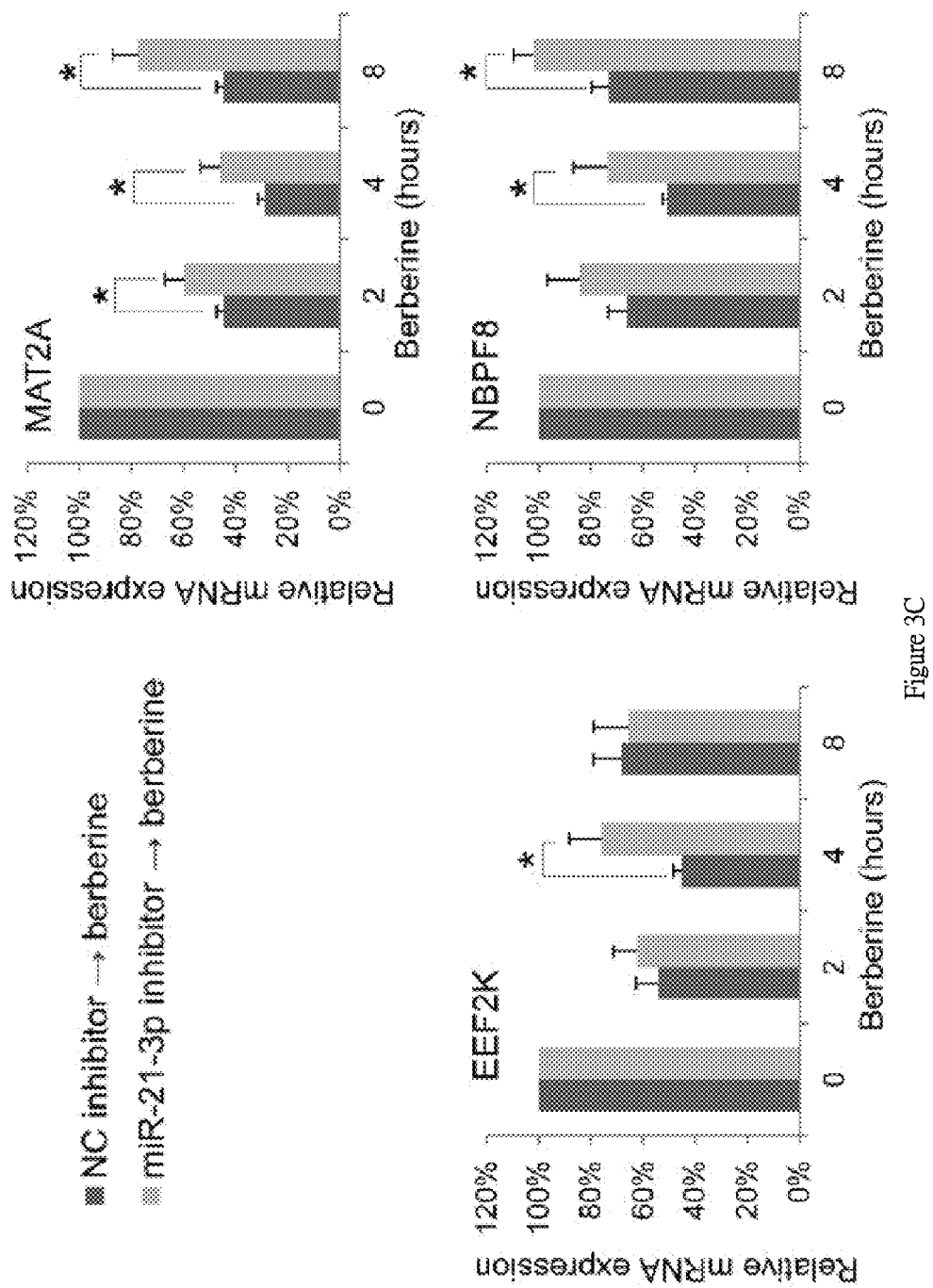
FIG. 3C represents the mRNA expression levels of HepG2 cells transfected with 100 nM of miR-21-3p hairpin inhibitor or negative-control (NC) inhibitor for 24 h, and then stimulated by the time course of 40 µM berberine treatment for 0-8 h. The mRNA expression is measured using qRT-PCR. The data are represented as the mean±standard deviation for 3 independent experiments. The asterisk mark "*" indicates a significant difference with $P<0.05$.
Figure 3C:
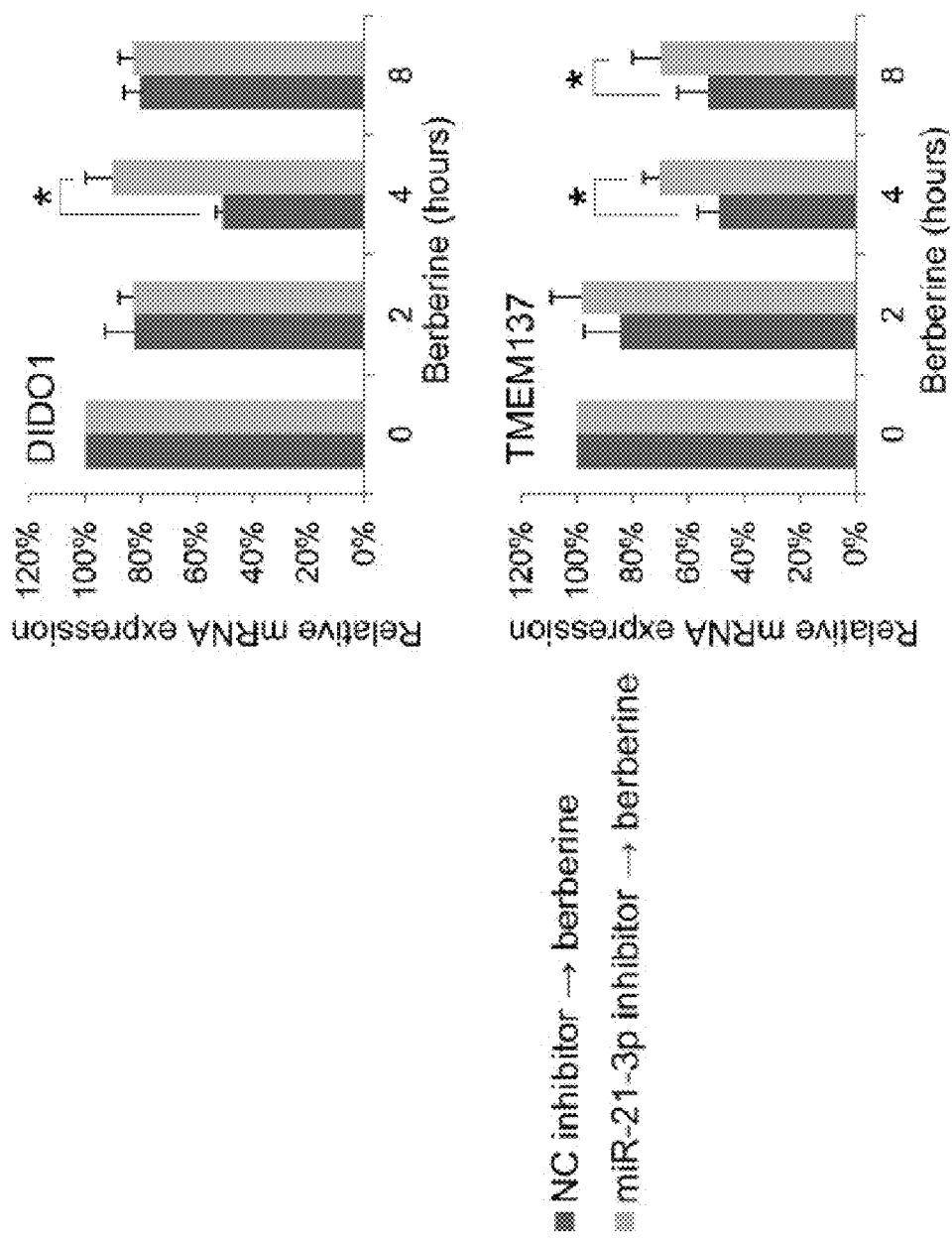

Identifying functionally important target genes of specific miRNA and understanding the mechanisms of their actions are essential to uncovering its biological function[58]. To predict the putative targets of miR-21-3p, we integrated the gene expression profiles of HepG2 cells after berberine treatment and compared them with the gene list that we generated from sequence-based miRNA target prediction software. As shown in FIG. 3A, the mRNA targets of miR-21-3p were predicted using the miRanda algorithm and an mirSVR score threshold of −0.1[59]. The predicted genes were overlapped with the microarray data of negatively regulated genes (more than a 1.5-fold decrease and P<0.05) after 40 μM berberine treatment for 4 h in HepG2 cells. Five gene targets, including MAT2A (methionine adenosyltransferase II, alpha), DIDO1 (death inducer-obliterator 1), EEF2K (eukaryotic elongation factor-2 kinase), NBPF8 (predicted: *Homo sapiens* neuroblastoma breakpoint family, member 8), and TMEM137 (predicted: *Homo sapiens* transmembrane protein 137) were identified using this prediction strategy. We next confirmed these predictions by performing gain-of-function and loss-of function experiments with miRNA mimics and inhibitors, and confirmed whether miRNA inhibitors could successfully rescue the berberine function in lowering the expression levels of selected targets. FIG. 3B shows that transfecting 50 nM of miR-21-3p mimics into HepG2 cells for 24 hours resulted in a >50% decrease in the mRNA expression of MAT2A and EEF2K, and a <50% decrease in the mRNA expression of DIDO1, NBPF8 and TMEM137. After the transfection of 100 nM of miR-21-3p hairpin inhibitor or negative-control inhibitor into HepG2 cells for 24 h, the cells were stimulated by the time course of 40 μM berberine treatment for up to 8 h compared with the untreated control. FIG. 3C shows that miR-21-3p inhibitor could successfully rescue the berberine function in the lowering mRNA expression levels of predicted targets. These results suggest that MAT1A, DIDO1, EEF2K, NBPF8, and TMEM137 were the targets of miR-21-3p. In the following experiments, we focused on methionine adenosyltransferase (MAT) which is strongly associated with hepatocellular carcinoma.

Example 4

Figure 4A:
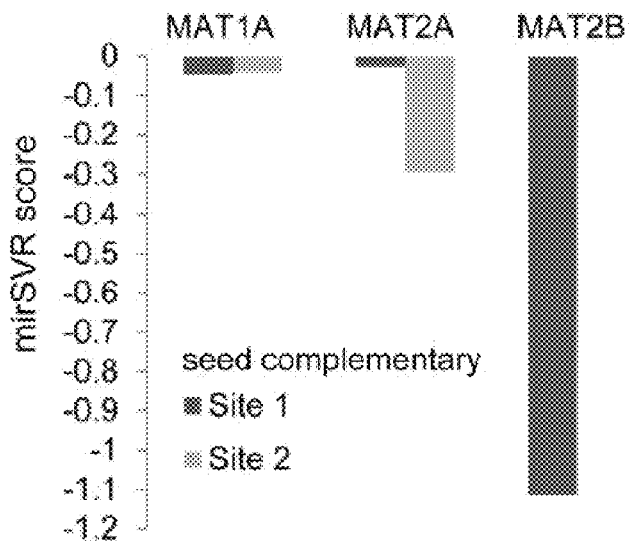
FIG. 4A represents the mirSVR score of each seed complementary site in the 3' UTRs of MAT1A, MAT2A and MAT2B.
Figure 4B:
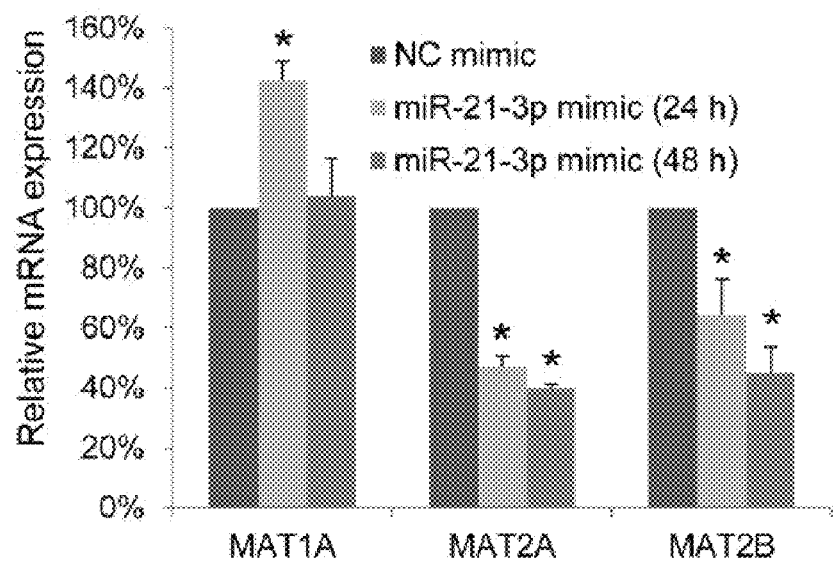
FIG. 4B represents the mRNA expression levels of MAT1A, MAT2A and MAT2B in HepG2 cells transfected with 50 nM of miR-21-3p mimic or negative-control (NC) mimic for 24 h and 48 h. The mRNA expression is measured using qRT-PCR. The data are represented as the mean±standard deviation for 3 independent experiments. The asterisk mark "*" indicates a significant difference with $P<0.05$.
Figure 4C:
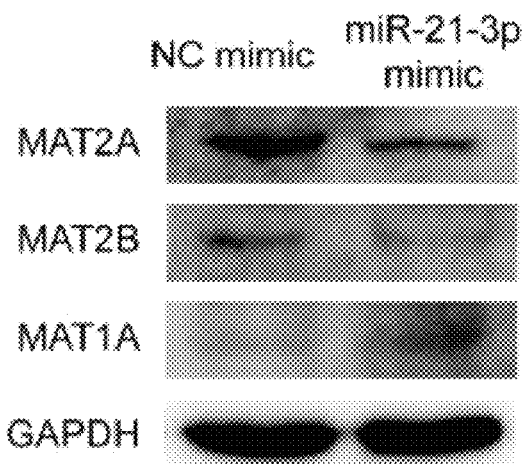
FIG. 4C represents the protein expression levels of MAT1A, MAT2A and MAT2B in HepG2 cells transfected with 50 nM of miR-21-3p mimic or negative-control mimic for 72 h. The protein expression is measured using Western blot analysis. GAPDH was used as the loading control.
Figure 4D:
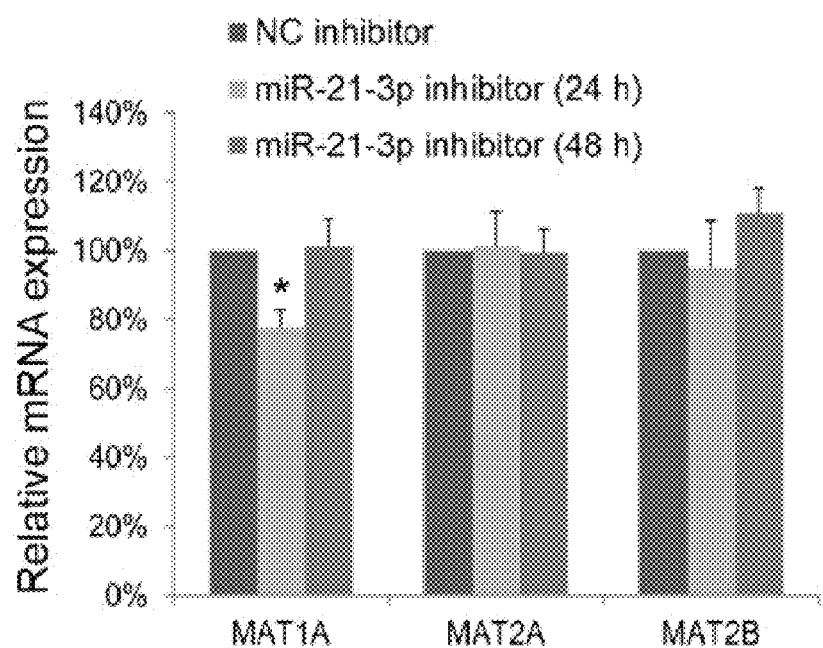
FIG. 4D represents the mRNA expression levels of MAT1A, MAT2A and MAT2B in HepG2 cells transfected with 100 nM of miR-21-3p inhibitor or negative-control (NC) inhibitor for 24 h and 48 h. The mRNA expression is measured using qRT-PCR. The data are represented as the mean±standard deviation for 3 independent experiments. The asterisk mark "*" indicates a significant difference with $P<0.05$.
Figure 4E:
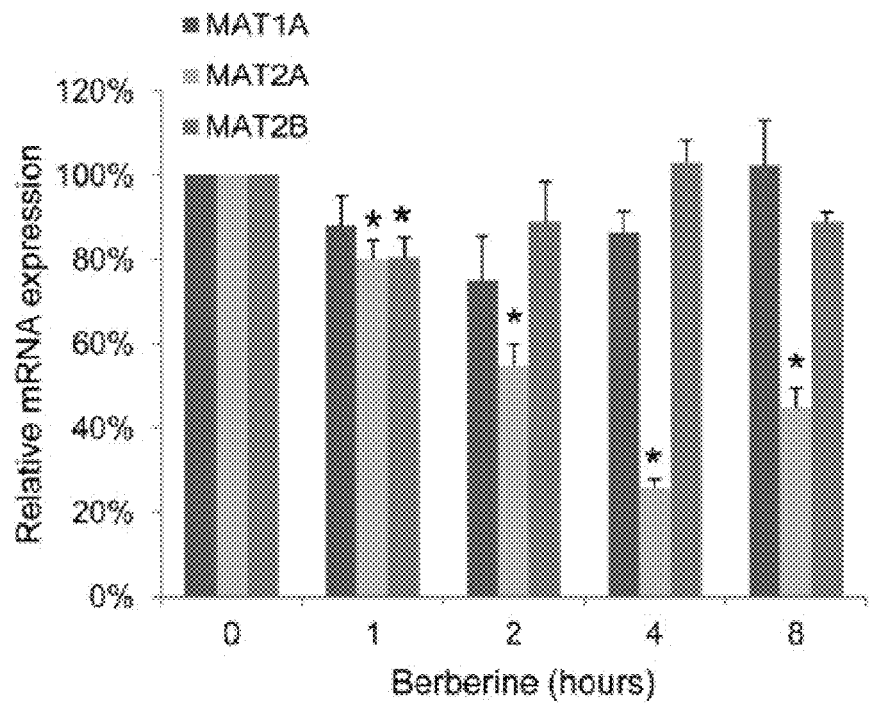
FIG. 4E represents the mRNA expression levels of MAT1A, MAT2A and MAT2B in HepG2 cells stimulated by the time course of 40 µM berberine treatment for up to 8 h compared with the untreated control. The mRNA expression is measured using qRT-PCR. The asterisk mark "*" indicates a significant difference with $P<0.05$.

MicroRNA-21-3p Reduces the Expression of Methionine Adenosyltransferases 2B and 2B After determining that MAT2A is the putative target of miR-21-3p, we investigated whether the expression levels of MAT family members including MAT1A, MAT2A, and MAT2B, could be altered by miR-21-3p. The histogram in FIG. 4A shows the miRanda-mirSVR scores of each seed complementary site in the 3' UTRs of MAT1A, MAT2A, and MAT2B. MAT2A and MAT2B scored lower than −0.1, suggesting that MAT2B might also be a target of miR-21-3p. To demonstrate the relationship between miR-21-3p and the expression levels of the MAT family, a miR-21-3p mimic or a negative-control mimic was transfected into HepG2 cells. The mRNA and protein expression levels of the MAT family members were subsequently assayed using qRT-PCR and western blotting. FIG. 4B shows that transfecting 50 nM of miR-21-3p mimic into HepG2 cells for 48 h resulted in a >50% decrease in the mRNA expression of MAT2A and MAT2B, but not in that of MAT1A. Furthermore, after the transfection of hsa-miR-21-3p mimic into HepG2 cells for 72 h, the protein expression levels of MAT2A and MAT2B showed a 2.6-fold and a 3.4-fold decrease, respectively. Furthermore, the MAT1A protein expression levels showed a 1.7-fold increase (FIG. 4C). By contrast, for the loss-of function experiments, the hairpin inhibitor of miR-21-3p were transfected into HepG2 cells to inhibit functions of endogenous miR-21-3p (with a negative control inhibitor as control). As shown in FIG. 4D, the MAT1A was 1.3-fold decreased by miR-21-3p inhibitor after transfection for 24 h, but not for 48 h. The expression levels of MAT2A and MAT2B remained unchanged after transfection for 24 h and 48 h. The MAT2B expression levels did not change notably according to our microarray data shown in FIG. 3A. To assess the relevance of berberine treatment and the expression levels of the MAT family members, qRT-PCR assays were used to measure mRNA expression in HepG2 cells stimulated by the time course of berberine treatment for up to 8 h compared with the untreated control (0.08% DMSO). As shown in FIG. 4E, MAT2A levels started to decreasing substantially by 2 h (1.8-fold decrease) after treatment, reached the lowest value at 4 h (3.8-fold decrease), and remained constant until 8 h (2.2-fold increase). The decreased levels of MAT2A were associated with higher miR-21-3p levels after berberine treatment for 2 h, 4 h, and 8 h, and the comparisons are shown in FIG. 1B. However, MAT1A and MAT2B expression levels did not change substantially which was consistent with our microarray data. Overall, our findings are the first evidence indicating that berberine treatment reduced MAT2A, and that the overexpression of miR-21-3p reduced the expression of both MAT2A and MAT2B.

Example 5

MicroRNA-21-3p Up-Regulates Intracellular SAM Contents in Hepatoma Cells

Figure 4F:
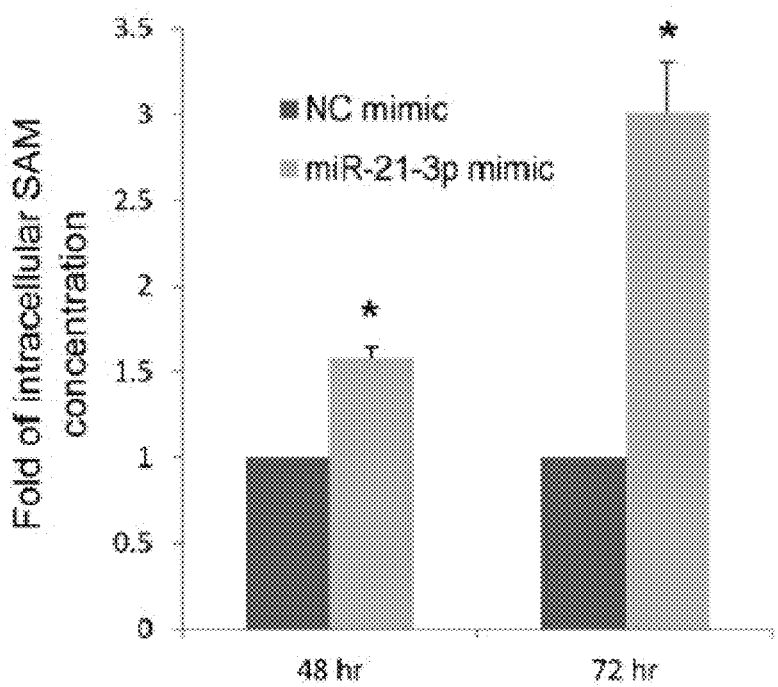
FIG. 4F represents the intracellular SAM concentration of the HepG2 cells transfected with 50 nM of miR-21-3p mimic or negative-control (NC) mimic for 72 h, which is shown in folds. The data are represented as the mean±standard deviation for 3 independent experiments. The asterisk mark "*" indicates a significant difference with $P<0.05$.

The increased expression of MAT2A and MAT2B in HCC results in decreasing SAM levels and facilitates cancer cell growth[6,7,15]. After determining that MAT2A and MAT2B are repressed by miR-21-3p, we analyzed the intracellular SAM contents in the HepG2 cell after transfection with miR-21-3p mimic and negative-control mimic as the control for 48 h and 72 h. As shown in FIG. 4F, the intracellular SAM contents were 1.6-fold and 3.0-fold increased by miR-21-3p mimic after transfection for 48 h and 72 h. These results indicate that the over-expression of miR-21-3p raised intracellular SAM contents, which have been proven to impair the growth of hepatoma cells.

Example 6

MAT2A and MAT2B are Direct Targets of miR-21-3p

Figure 5A:
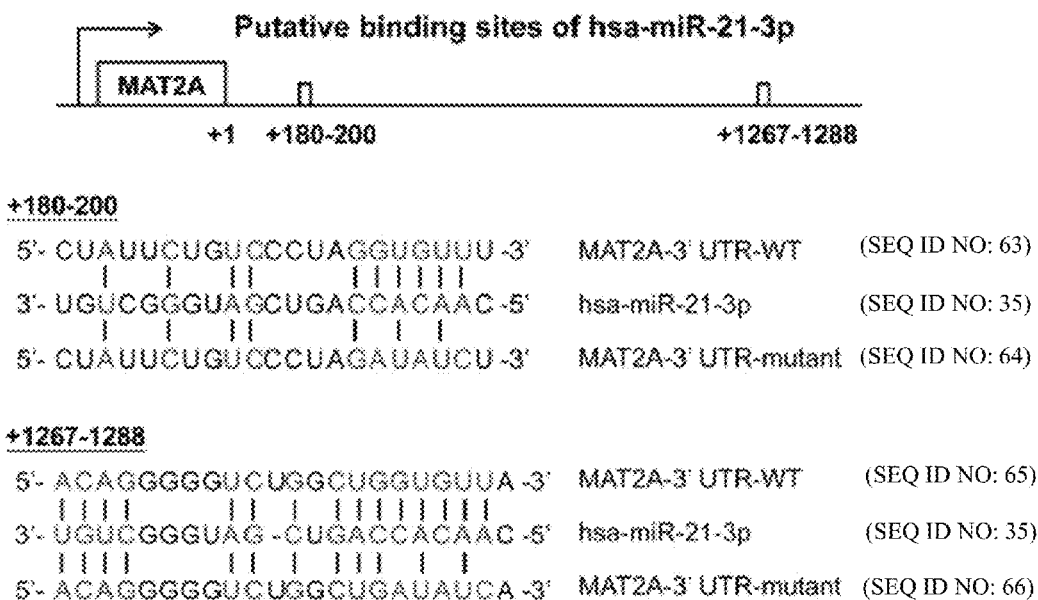
FIG. 5A is a schematic representation showing the putative 3' UTR binding sites of MAT1A (SEQ ID No: 63 to SEQ ID No: 66) for hsa-miR-21-3p.
Figure 5B:
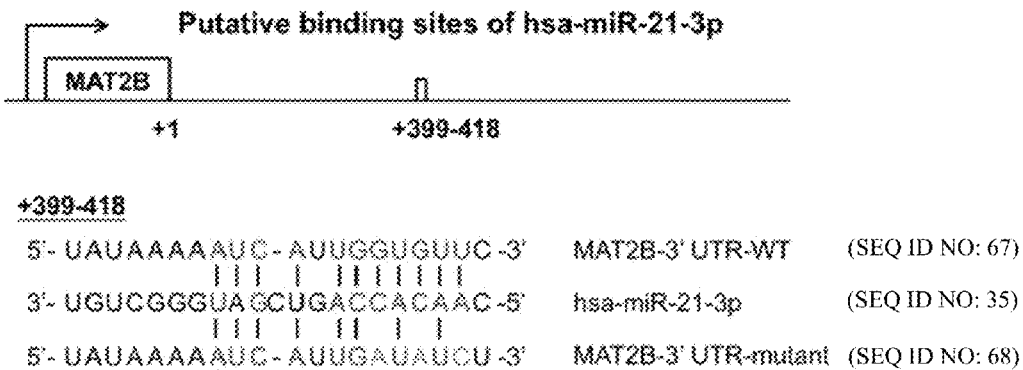
FIG. 5B is a schematic representation showing the putative 3' UTR binding sites of MAT2B (SEQ ID No: 67 to SEQ ID No: 68) for hsa-miR-21-3p.
Figure 5C:
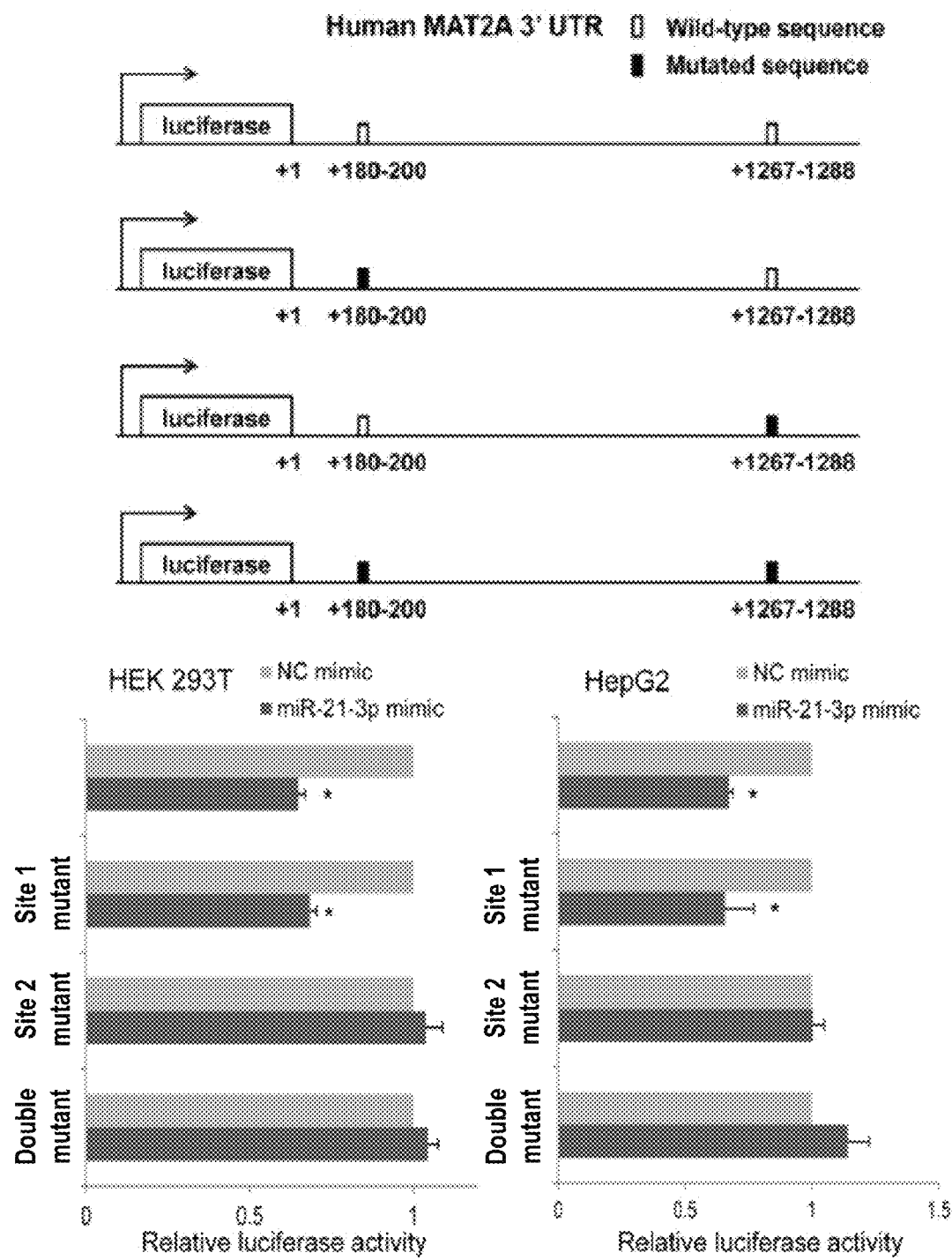
FIG. 5C is a schematic representation showing the mutated seed binding sites in 3' UTR of MAT2A, which inserted downstream of the luciferase of the pMIR-reporter vector. It also shows the luciferase activity of HEK293T and HepG2 cells tri-transfected with either wild-type or mutant pMIR-reporter vector, the Renilla luciferase reporter plasmid pRL-TK, and either hsa-miR-21-3p mimic or negative-control mimic. The data are represented as the mean±standard deviation for 3 independent experiments. The asterisk mark "*" indicates a significant difference with $P<0.05$.
Figure 5D:
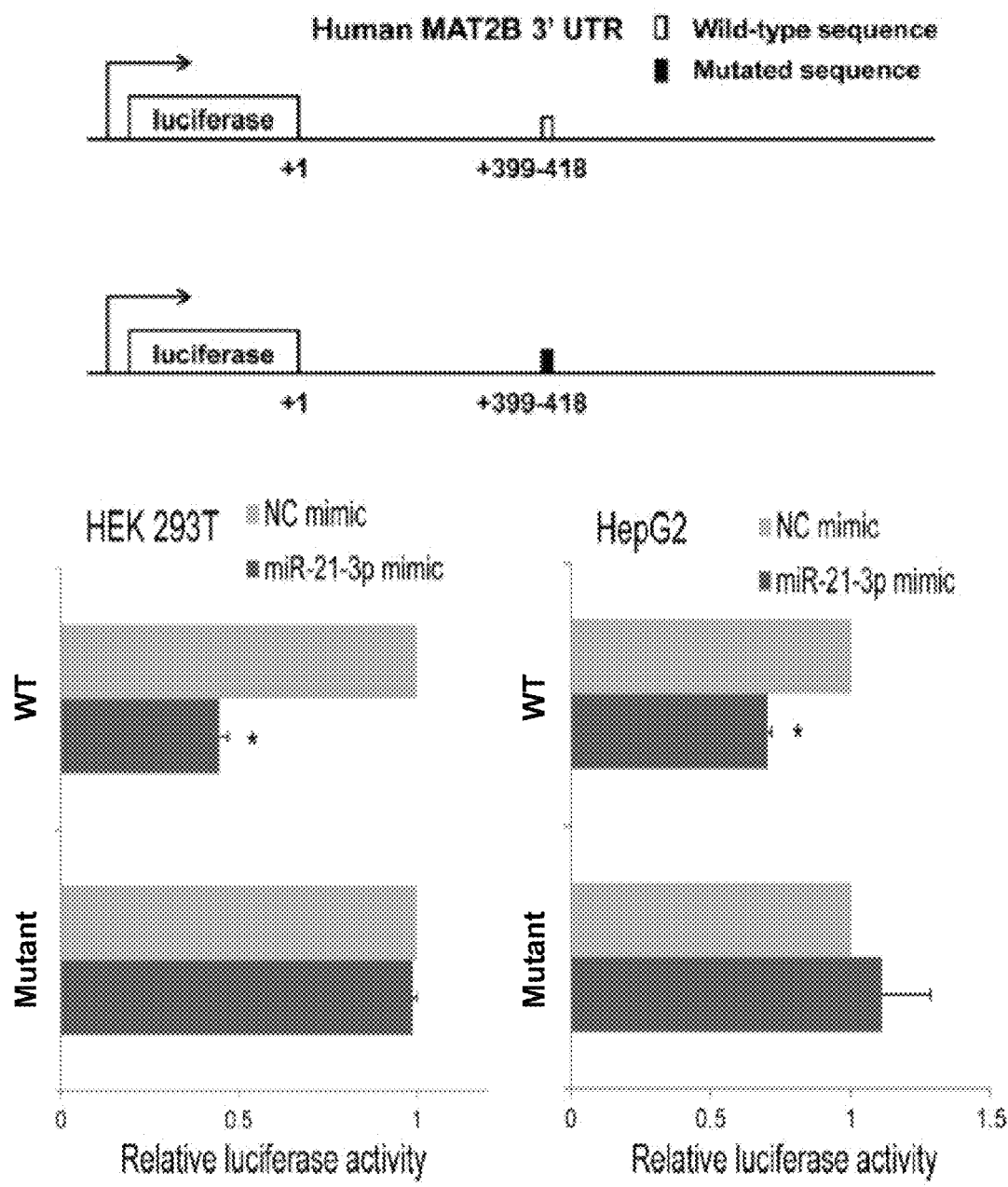
FIG. 5D is a schematic representation showing the mutated seed binding sites in 3' UTR of MAT2B, which inserted downstream of the luciferase of the pMIR-reporter vector. It also shows the luciferase activity of HEK293T and HepG2 cells tri-transfected with either wild-type or mutant pMIR-reporter vector, the Renilla luciferase reporter plasmid pRL-TK, and either hsa-miR-21-3p mimic or negative-control mimic. The data are represented as the mean±standard deviation for 3 independent experiments. The asterisk mark "*" indicates a significant difference with $P<0.05$.

Because MAT2A and MAT2B decreased after miR-21-3p mimic transfection, we investigated the relevance of miR-21-3p and the 3' UTRs of MAT2A and MAT2B. Full-length wild-type or mutant 3' UTRs of MAT2A and MAT2B were separately cloned into luciferase reporter vectors (FIGS. 5A and 5B, respectively), and the dual luciferase reporter assay system was used to quantitate the reporter activity. FIG. 5C shows that miR-21-3p suppressed the expression (a 1.6-fold decrease in HEK 293T cells and a 1.5-fold decrease in HepG2 cells) of the luciferase reporter containing the MAT2A 3' UTR, suggesting that miR-21-3p directly regulates the MAT2A 3' UTR. To confirm whether the miR-21-3p cleaves the MAT2A 3' UTR through miRNA:mRNA seed pairing, the site-directed mutagenesis of the putative miR-21-3p binding sequence on the MAT2A 3' UTR was performed. By using MicroRNA.org (http://www.microrna.org), a comprehensive resource of microRNA target predictions, miR-21-3p was predicted to target 2 sites (Site 1: +180-200 and Site 2: +1267-1288) in the 3' UTR of MAT2A. The results show that miR-21-3p suppressed the expression (a 1.5-fold decrease in both HEK 293T cells and HepG2 cells) of the luciferase reporter containing Site 1 mutated MAT2A 3' UTR. Conversely, the expression levels of the luciferase reporter containing Site 2 mutated MAT2A 3' UTR did not notably change, similar to the reporter containing the double-mutated (both Site 1 and Site 2) MAT2A 3' UTR. This suggests that Site 2 (+1267-1288) in the MAT2A 3' UTR is the major cleavage site of miR-21-3p (FIG. 5C). In addition, miR-21-3p was predicted to target one seed match (+399-418) in the 3' UTR of MAT2B. As shown in FIG. 5D, miR-21-3p suppressed the expression (a 2.3-fold decrease in HEK 293T cells and a 1.4-fold decrease in HepG2 cells) of the luciferase reporter containing the MAT2B 3' UTR, but the expression levels of the luciferase reporter containing the mutated MAT2B 3' UTR remained unchanged in both HEK 293T cells and HepG2 cells. This suggests that the seed match (+399-418) in the MAT2B 3' UTR is the major cleavage site of miR-21-3p. These results showed that MAT2A and MAT2B are both direct targets of miR-21-3p.

Example 7

MicroRNA-21-3p Suppresses Growth and Induces Apoptosis in Hepatoma Cells

Figure 6A:
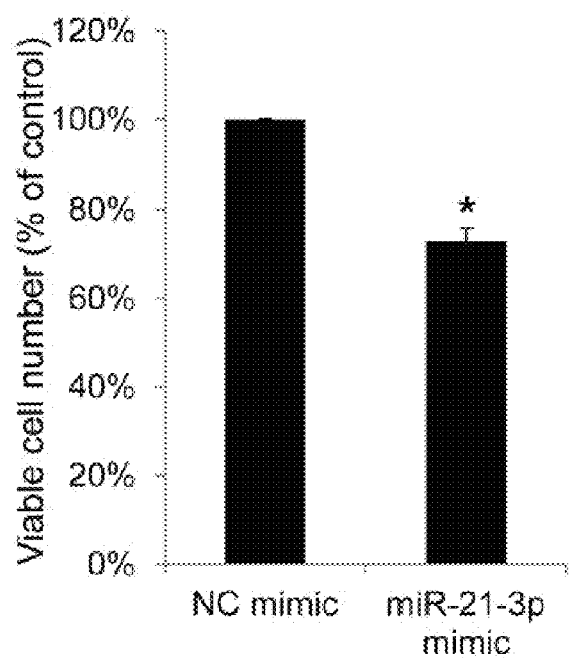
FIG. 6A represents the number of viable HepG2 cells transfected with 50 nM of miR-21-3p mimic or negative-control (NC) mimic for 48 h, which is quantified using trypan blue dye exclusion assay. The data are represented as the mean±standard deviation for 3 independent experiments. The asterisk mark "*" indicates a significant difference with $P<0.05$.
Figure 6B:
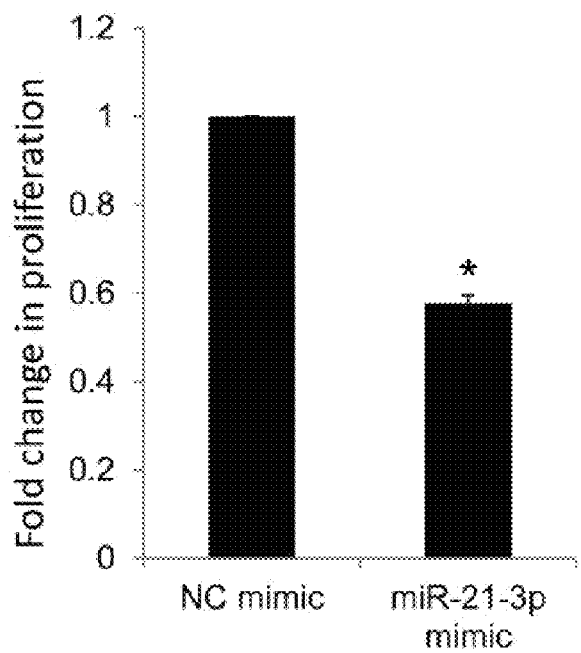
FIG. 6B represents the cellular proliferation (shown in folds) of HepG2 cells transfected with 50 nM of miR-21-3p mimic or negative-control (NC) mimic for 24 h and then incubated with BrdU for an additional 24 h, which is measured using BrdU incorporation assay. The data are represented as the mean±standard deviation for 3 independent experiments. The asterisk mark "*" indicates a significant difference with $P<0.05$.
Figure 6C:
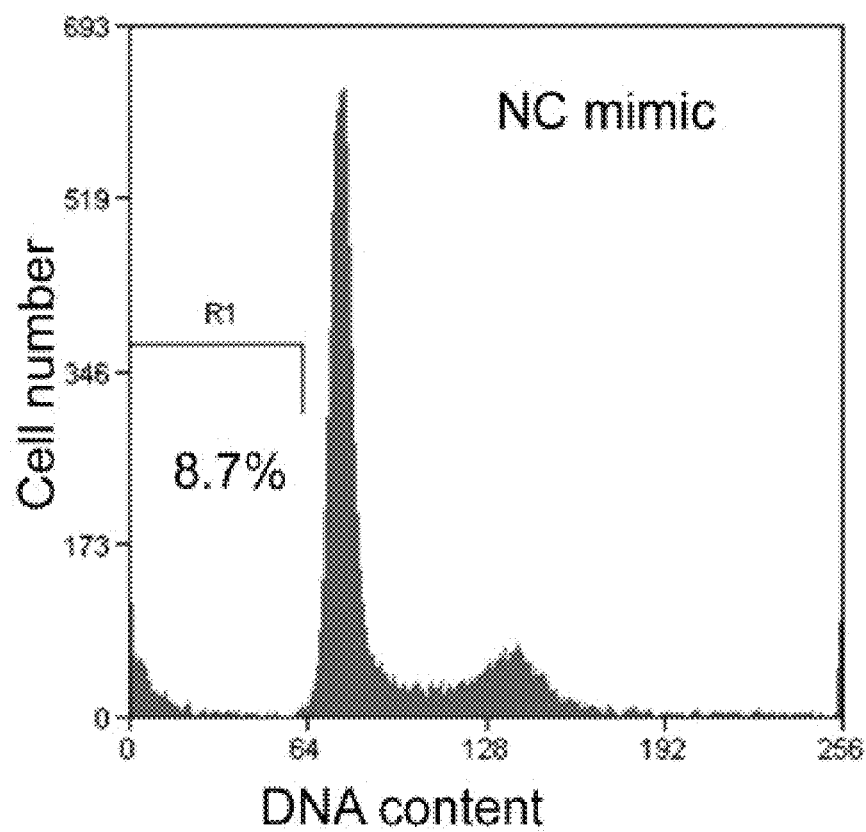
FIG. 6C represents the apoptotic cell population of HepG2 cells transfected with negative-control (NC) mimic for 72 h, which is detected using flow cytometry.
Figure 6D:
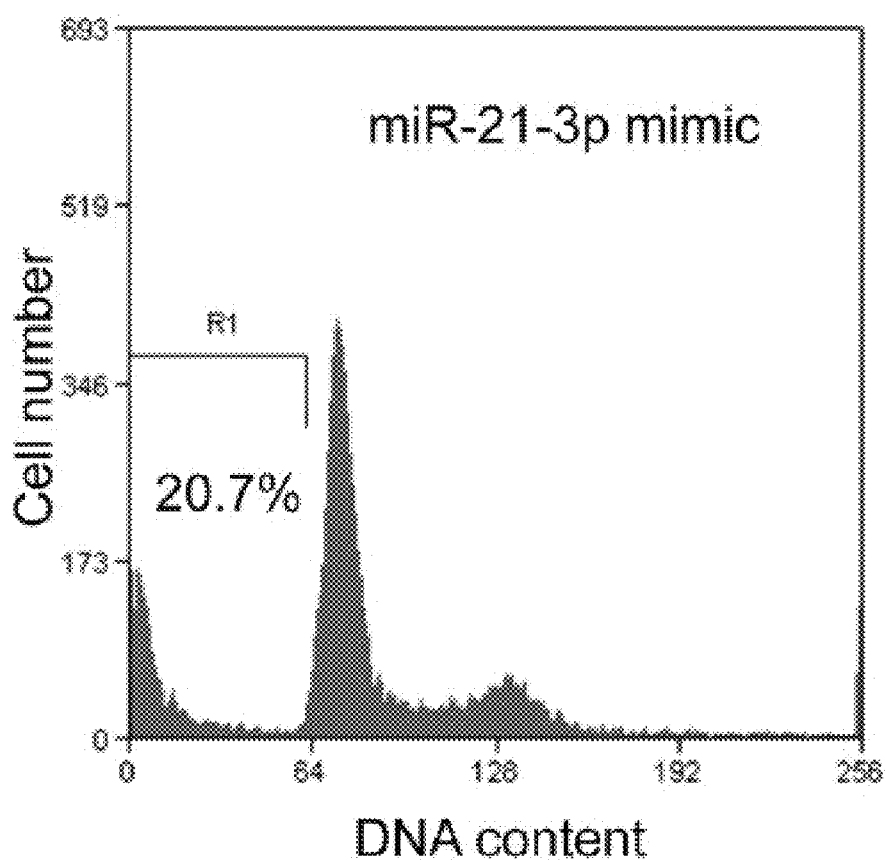
FIG. 6D represents the apoptotic cell population of HepG2 cells transfected with 50 nM of miR-21-3p mimic for 72 h, which is detected using flow cytometry.
Figure 6E:
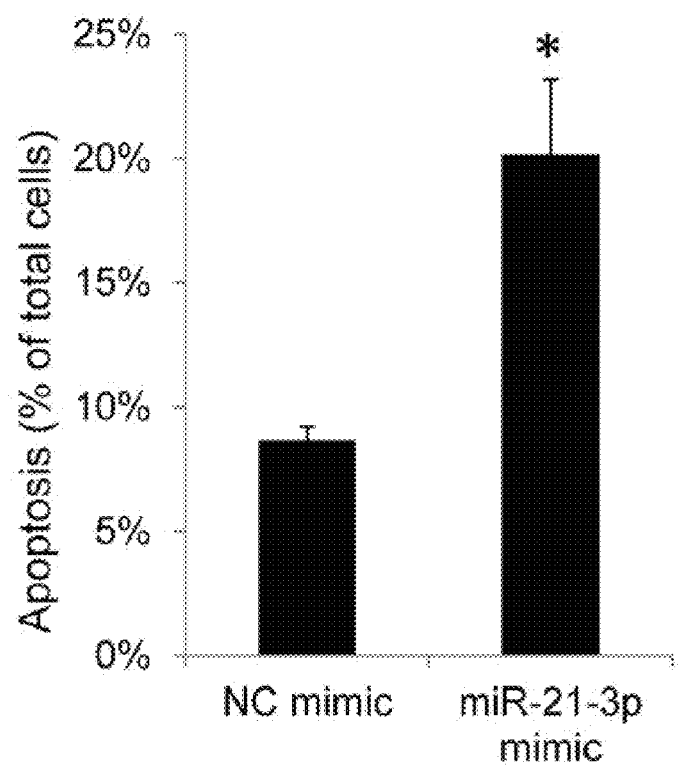
FIG. 6E shows the quantified comparison of FIGS. 6C and 6D. The data are represented as the mean±standard deviation for 3 independent experiments. The asterisk mark "*" indicates a significant difference with $P<0.05$.

To investigate the potential effects of miR-21-3p on cell growth and viability, we measured cell proliferation and viability by using the BrdU incorporation assay and the Trypan blue dye exclusion assay. The results shown in FIG. 6A indicate that miR-21-3p mimic reduced the viable cell numbers in HepG2 cells after transfection for 48 h. In addition, transfecting miR-21-3p mimic into HepG2 cells for 24 h and incubation for an additional 24 h for BrdU incorporation led to the inhibition of cellular proliferation (1.7-fold), compared with transfection with negative-control mimic (FIG. 6B). The effects of miR-21-3p on apoptosis and the cell cycle were evaluated using flow cytometry analysis. After HepG2 cells transfection with miR-21-3p and negative-control mimic as the control for 72 h, the sub-G1 populations of apoptotic cells were quantified. As shown in FIGS. 6C, 6D, and 6E, miR-21-3p induced apoptosis in HepG2 cells.

Example 8

Figure 7A:
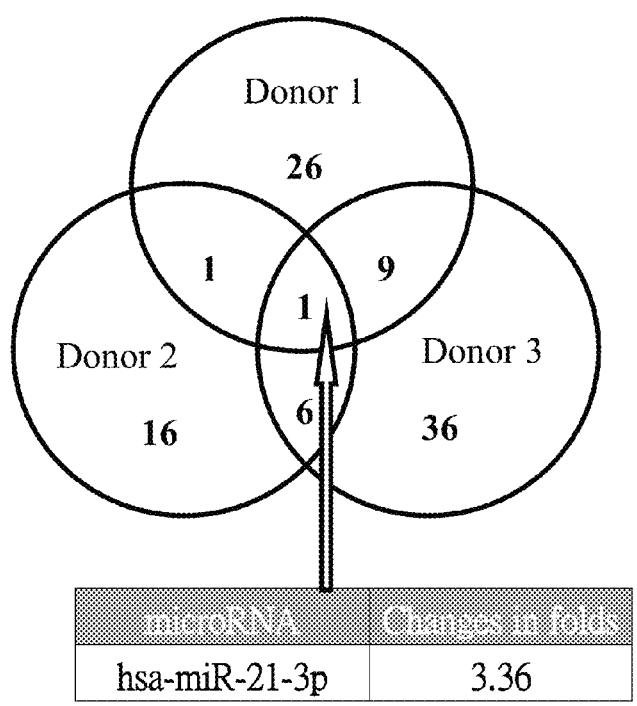
FIG. 7A represents the microRNAs that change >1.5 fold in PHH cells at 2 h following 40 µM berberine treatment (compared with the untreated PHH cells), which is obtained from microarray results. Only the expression of hsa-miR-21-3p increases in all PHH cells obtained from the 3 donors.
Figure 7B:
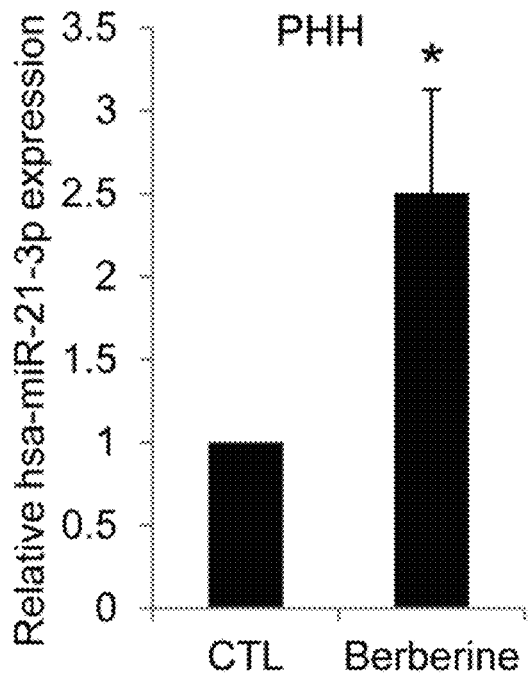
FIG. 7B represents the mRNA expression levels of hsa-miR-21-3p in PHH cells at 2 h following 40 μM berberine treatment and untreated PHH cells (CTL), which is measured by qRT-PCR. The data are represented as the mean±standard deviation for independent experiments using PHH cells from 3 donors. *P<0.05.

MicroRNA-21-3p Reduces Lipid Droplet Content and Induces Apoptosis in Hepatic Cells The isoquinoline alkaloid berberine has a wide range of pharmacological effects, including its lipid-lowering effect in alleviating fatty liver syndrome in vivo[54-58]. Using the method the same as that used in Example 1, we employed a microRNA array to determine whether berberine treatment changed the microRNA among non-transformed human hepatocytes. The microRNA profiles of berberine-treated (40 μM) primary human hepatocytes (PHHs) from 3 overweight or obese male donors were compared with those of control group samples, which were obtained 2 h following treatment. Among the 3 donor microRNA profiles, we observed a consistent increase in only hsa-miR-21-3p expression (mean=3.36-fold; FIG. 7A). The up-regulation of miR-21-3p by berberine treatment in the PHHs was confirmed based on a qRT-PCR (FIG. 7B).

Figure 7C:
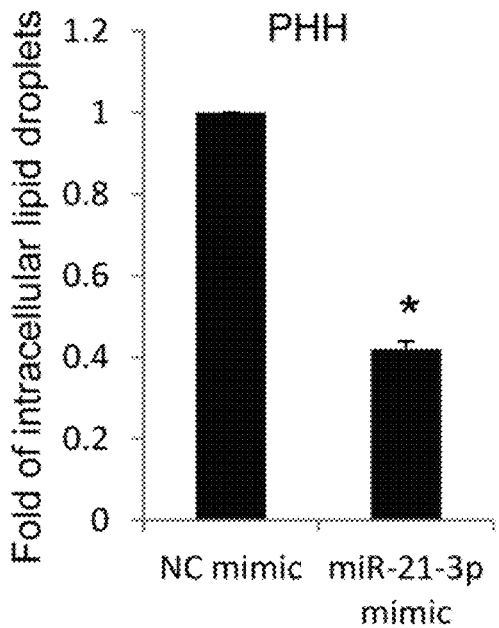
FIG. 7C represents the intracellular lipid droplet contents in PHH cells transfected with 50 nM of hsa-miR-21-3p mimic or negative-control (NC) mimic for 72 h, which are shown in folds. The data are represented as the mean±standard deviation for independent experiments using PHH cells from 3 donors. *P<0.05.

We employed flow cytometry, using BODIPY 493/503 staining[59] to examine the effect of miR-21-3p on the hepatic lipid droplet content. Among the PHH samples, the over-expression of miR-21-3p resulted from transfection of miR-21-3p mimic of the present invention caused a reduction in the intracellular lipid droplet content at 72 h (40% to 44% of the lipid droplet content among the control samples), as shown in FIG. 7C.

Figure 7D:
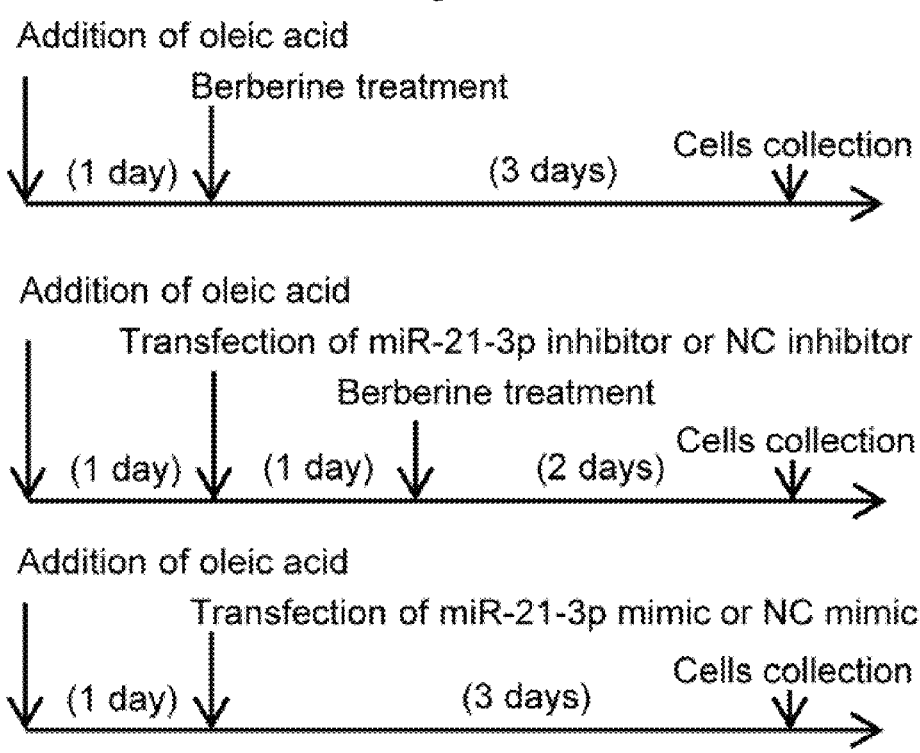
FIG. 7D represents the experimental procedures using HepG2 cells as the in vitro liver model for the fat droplet formation induced by oleic acid.

The up-regulation of miR-21-3p in PHHs is consistent with the result of Example 1, which shows that miR-21-3p increased in the human HepG2 hepatoma cell line after berberine treatment. Therefore, we used an oleic acid-induced in vitro fatty liver model for HepG2 cells to examine the relationship between hepatic steatosis and berberine-induced miR-21-3p[60, 61]. FIG. 7D shows the timeline for experiment procedures, in which the group 1 was treated with oleic acid for 24 h (1 day) to induce intracellular lipid droplet formation, and then treated with 40 μM berberine for 72 h (3 days); the group 2 was treated with oleic acid for 24 h (1 day) to induce intracellular lipid droplet formation first, then treated with 100 nM miR-21-3p hairpin inhibitor or negative-control (NC) inhibitor for 24 h (1 day), and then treated with 40 μM berberine for 48 h (2 days); and the group 3 was treated with oleic acid for 24 h (1 day) to induce intracellular lipid droplet formation first, and then treated with 50 nM miR-21-3p mimic or negative-control (NC) mimic for 72 h (3 days). After the above treatments, cell samples were collected separately, and the intracellular lipid droplet contents of the HepG2 cells were detected by flow cytometry.

Figure 7E:
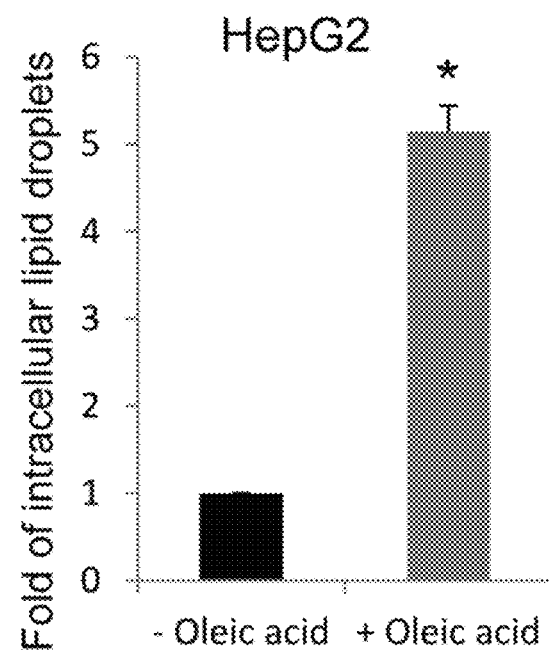
FIG. 7E represents intracellular lipid droplet contents in HepG2 cells induced by 200 μM oleic acid to form fat droplet and the untreated HepG2 cells. The data are represented as the mean±standard deviation for 3 independent experiments. The asterisk mark "*" indicates a significant difference with P<0.05.
Figure 7F:
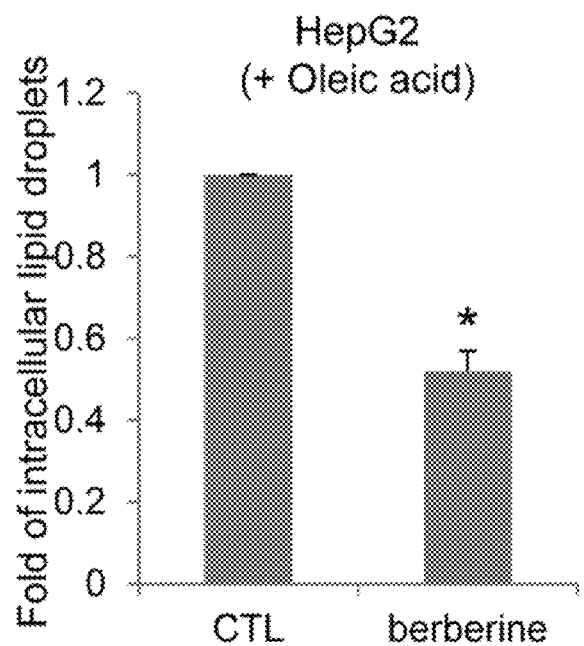
FIG. 7F represents intracellular lipid droplet contents in HepG2 cells induced by oleic acid to form fat droplet and then treated with 40 μM berberine treatment for 72 h (compared with the untreated HepG2 cells). The data are represented as the mean±standard deviation for 3 independent experiments. The asterisk mark "*" indicates a significant difference with P<0.05.
Figure 7G:
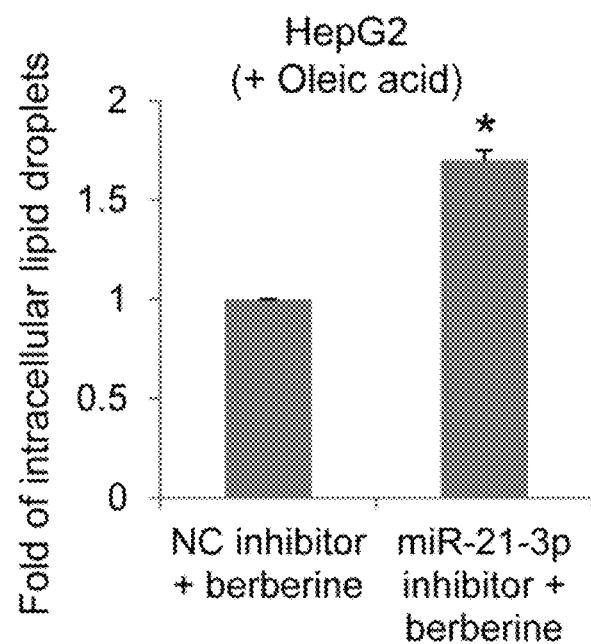
FIG. 7G represents intracellular lipid droplet contents in HepG2 cells induced by oleic acid to form fat droplet, transfected with 100 nM miR-21-3p hairpin inhibitor or negative-control (NC) inhibitor for 24 h, and then treated with 40 μM berberine treatment for 48 h (compared with the untreated HepG2 cells). The data are represented as the mean±standard deviation for 3 independent experiments. The asterisk mark "*" indicates a significant difference with P<0.05.
Figure 7H:
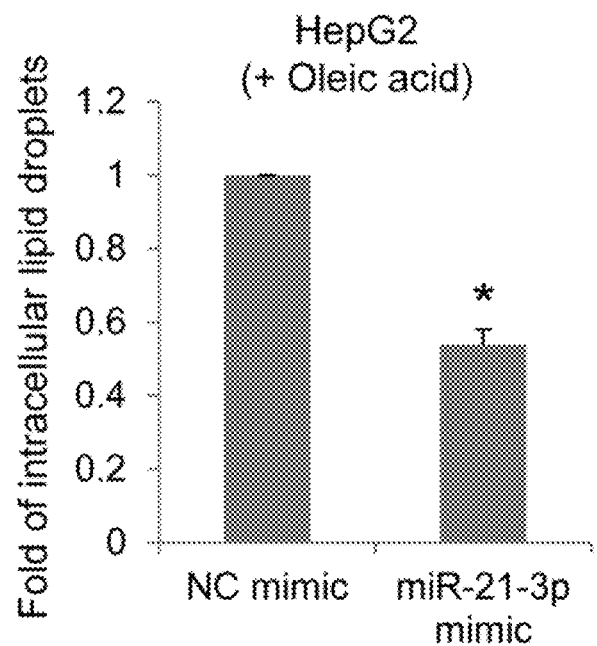
FIG. 7H represents intracellular lipid droplet contents in HepG2 cells induced by oleic acid to form fat droplet, transfected with 50 nM miR-21-3p mimic or negative-control (NC) mimic for 72 h. The data are represented as the mean±standard deviation for 3 independent experiments. The asterisk mark "*" indicates a significant difference with P<0.05.

FIG. 7E shows that lipid-accumulated cells mimicking hepatic steatosis were successfully induced in the HepG2 cells by adding oleic acid. In this cell model, the 72-h berberine treatment reduced the lipid droplet content (47% to 57% of the lipid droplet content among the untreated control samples) (FIG. 7F). In addition, FIG. 7G shows that after inhibiting endogenous miR-21-3p by the transfection of miR-21-3p inhibitor, the lipid droplet content cannot be reduced because the miR-21-3p induced by berberine is inhibited by the inhibitor. This demonstrates that berberine induces miR-21-3p to reduce intracellular lipid droplet content. Furthermore, the over-expression of miR-21-3p caused a reduction in the lipid droplet content (50% to 58% of the lipid droplet content among the control group samples) (FIG. 7H). Similar results were obtained in the HepG2 cells, despite a lack of oleic acid-induction (data not shown). Overall, these results indicate that miR-21-3p decreases hepatic lipid droplet content.

Example 9

Prediction and Confirmation of Targets of MicroRNA-21-3p in Primary Liver Cells

Figure 8:
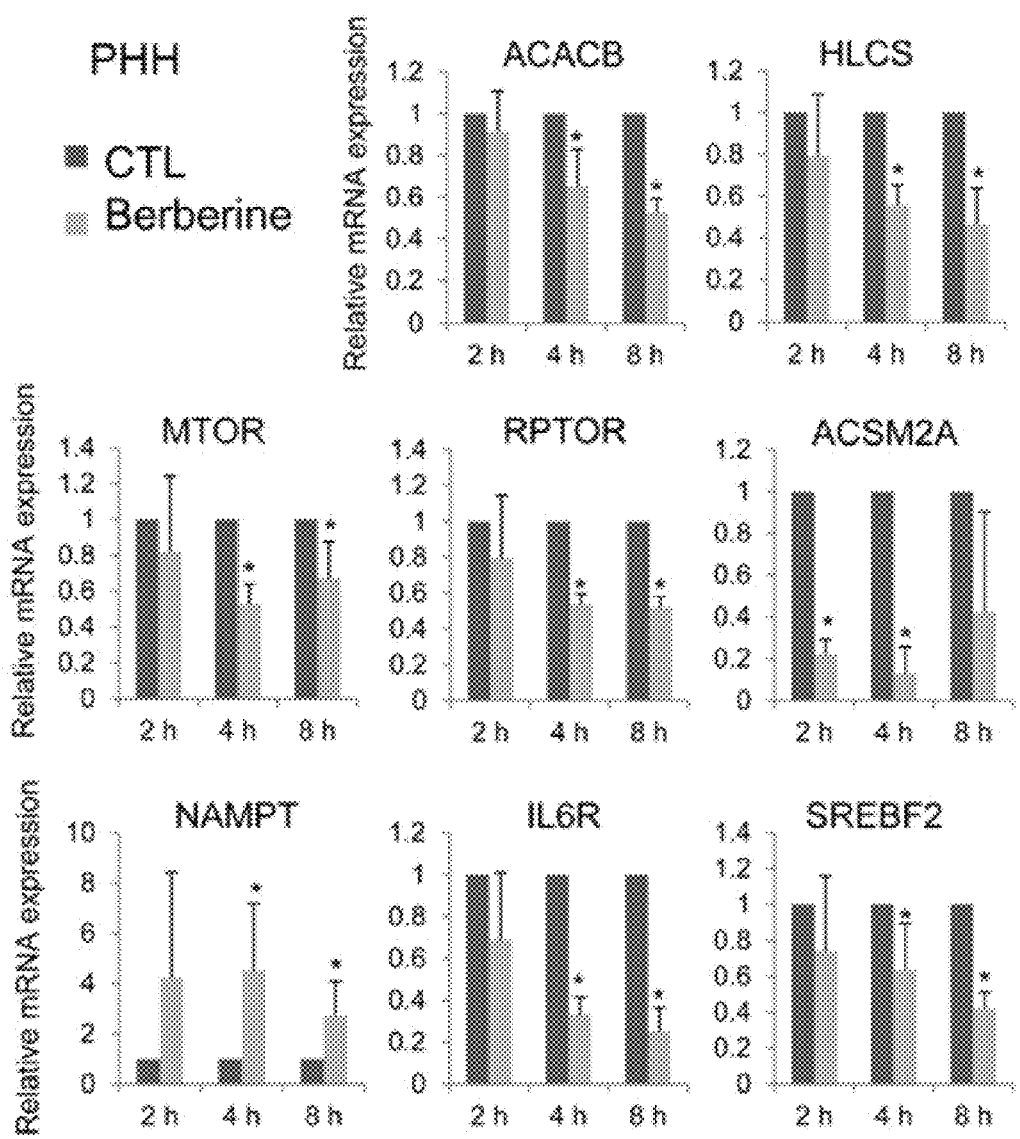
FIG. 8 represents the mRNA expression levels of lipid metabolic genes in PHH cells stimulated by 40 μM berberine treatment for 2 h, 4 h and 8 h (compared with the untreated PHH cells, CTL), in which the data is shown in folds. The data are represented as the mean±standard deviation for independent experiments using PHH cells from 4 donors. The asterisk mark "*" indicates a significant difference with P<0.05.

To identify which lipid metabolic genes were regulated by berberine, we examined the time course (2, 4, and 8 h) expression profiles of the berberine-treated (40 μM) and untreated PHHs from 3 overweight or obese male donors. The relative mRNA expression levels of the 8 selected genes, including ACACB, HLCS, MTOR, RPTOR, ACSM2A, NAMPT, IL6R and SPEBF2, were further validated (FIG. 8). It was found that the mRNA expression of ACACB, HLCS, MTOR, RPTOR, IL6R, and SPEBF2 decreases during the 4-8-h, and that of ACSM2A considerably decreases during the 2-4 h period. By contrast, an increase in the mRNA expression of NAMPT was observed during the 4-8 h period after berberine treatment. Subsequently, we examined the expression of these genes in HepG2 cells, and found that only ACACB consistently decreased in the HepG2 cells and PHHs (data not shown). Subsequently, we focused on acetyl-CoA carboxylase in the following experiments.

Figure 9A:
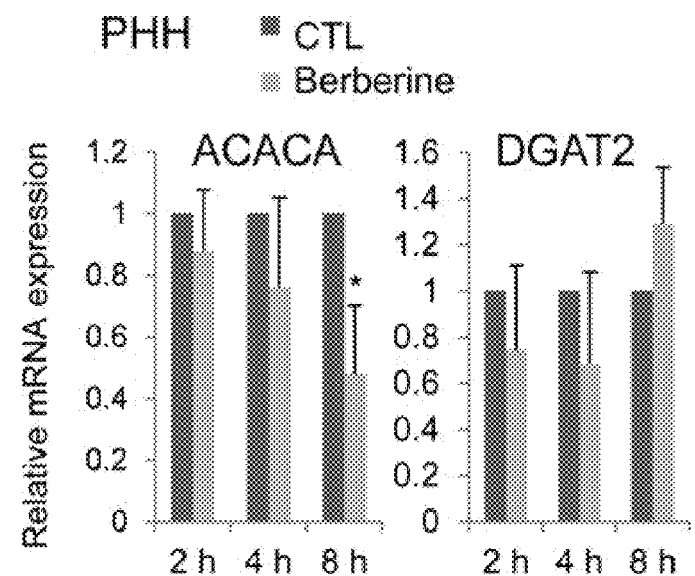
FIG. 9A represents the mRNA expression levels of ACACA and DGAT2 in PHH cells stimulated by 40 μM berberine treatment for 2 h, 4 h and 8 h (compared with the untreated PHH cells, CTL), in which the data is shown in folds. The data of ACACA are represented as the mean±standard deviation for independent experiments using PHH cells from 4 donors; and the data of DGAT2 are represented as the mean±standard deviation for independent experiments using PHH cells from 3 donors. The asterisk mark "*" indicates a significant difference with P<0.05.
Figure 9B:
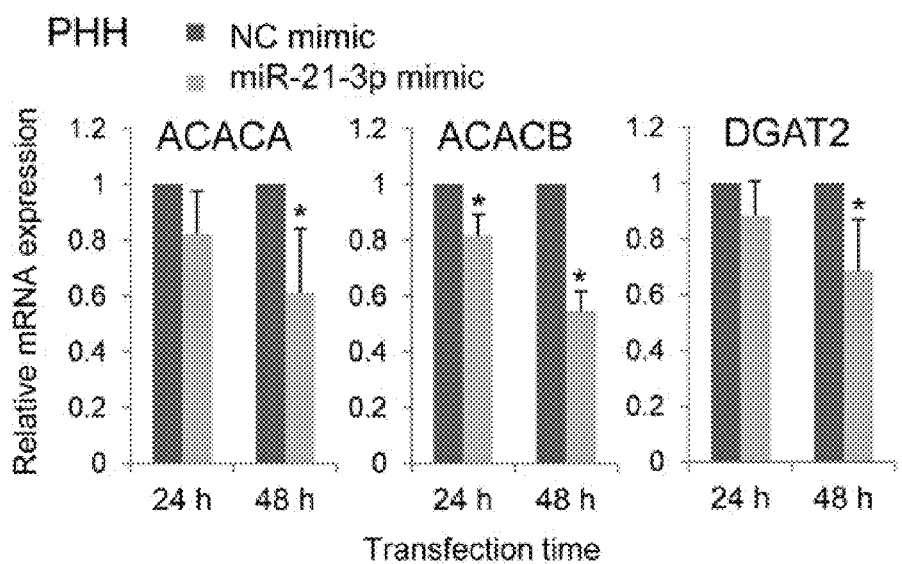
FIG. 9B represents the mRNA expression levels of ACACA, ACACB and DGAT2 in PHH cells transfected with 50 nM miR-21-3p mimic or negative-control (NC) mimic for 24 h and 48 h, in which the data is shown in folds. The data are represented as the mean±standard deviation for independent experiments using PHH cells from 3 donors. The asterisk mark "*" indicates a significant difference with P<0.05.
Figure 9C:
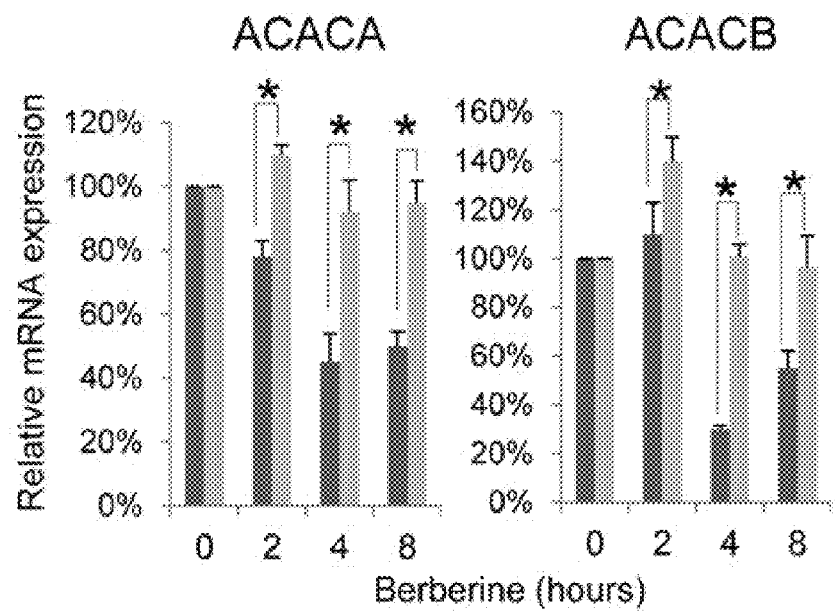
FIG. 9C represents the mRNA expression levels of ACACA, ACACB and DGAT2 in HepG2 cells transfected with 100 nM miR-21-3p hairpin inhibitor or negative-control (NC) inhibitor for 24 h, and then stimulated with 40 μM berberine treatment for 0-8 h, in which the data is shown in folds. The data are represented as the mean±standard deviation for independent experiments using PHH cells from 3 donors. The asterisk mark "*" indicates a significant difference with P<0.05.
Figure 9D:
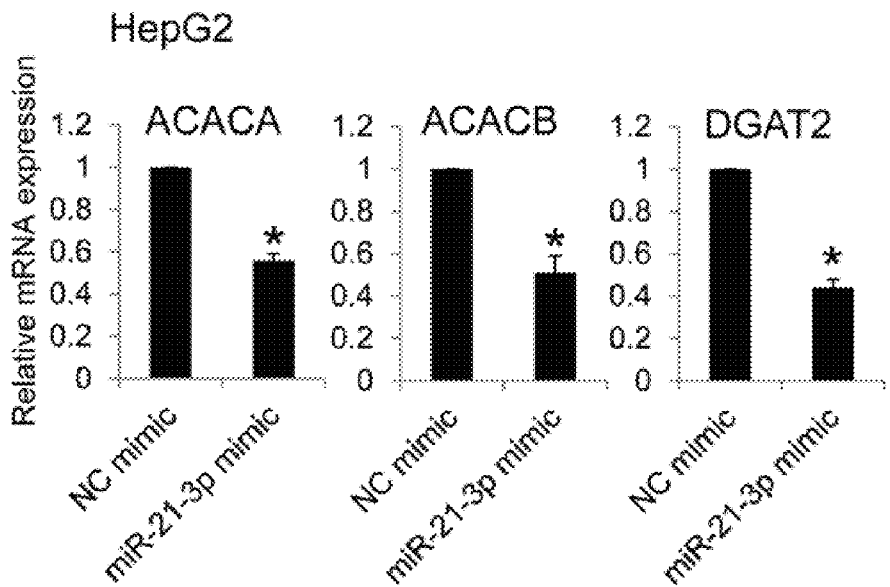
FIG. 9D represents the mRNA expression levels of ACACA, ACACB and DGAT2 in HepG2 cells transfected with 50 nM miR-21-3p mimic or negative-control (NC) mimic for 24 h, in which the data is shown in folds. The data are represented as the mean±standard deviation for independent experiments using PHH cells from 3 donors. The asterisk mark "*" indicates a significant difference with P<0.05.
Figure 9E:
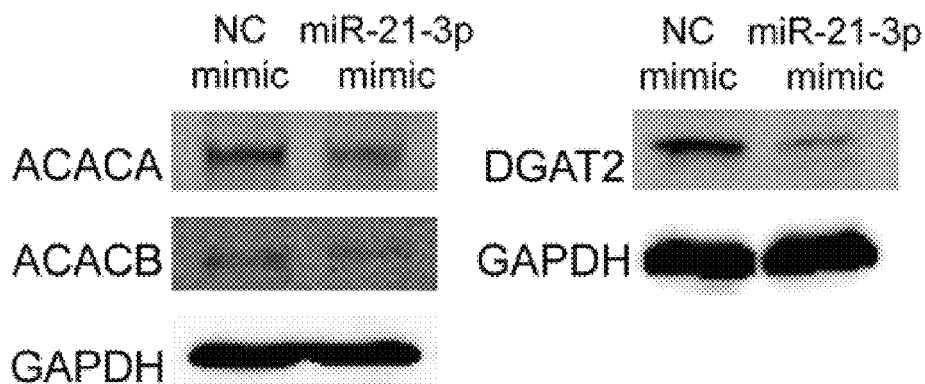
FIG. 9E represents the protein expression levels of ACACA, ACACB and DGAT2 in HepG2 cells transfected with 50 nM miR-21-3p mimic or negative-control (NC) mimic for 72 h.
Figure 9F:
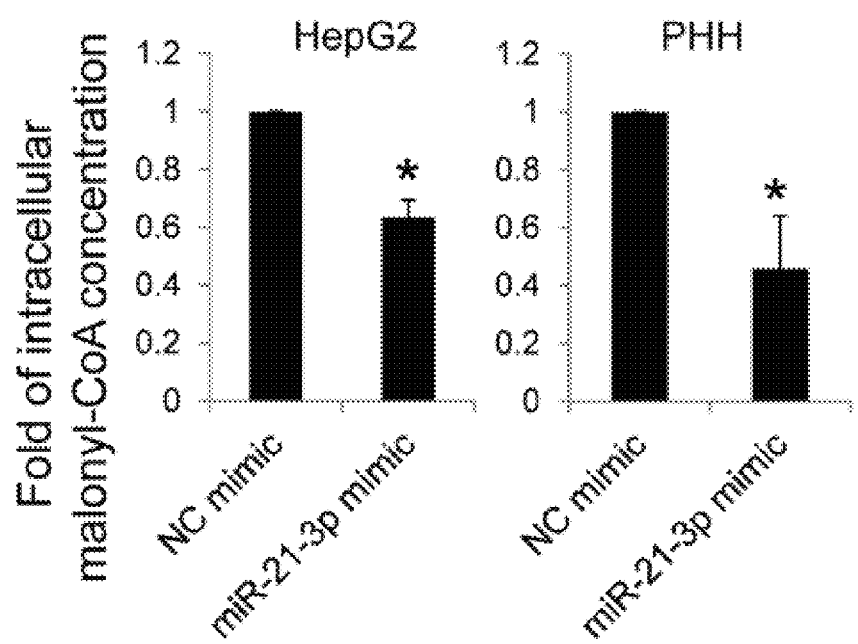
FIG. 9F represents the intracellular malonyl-CoA concentration in HepG2 and PHH cells transfected with 50 nM miR-21-3p mimic or negative-control (NC) mimic for 72 h, in which the data is shown in folds. The data are represented as the mean±standard deviation for independent experiments using PHH cells from 3 donors. *P<0.05.

Although ACACA was not extracted from the microarray data, we observed a 2.1-fold decrease in ACACA expression among the 3 donor samples at 8 h after berberine treatment (FIG. 9A). Next, we examined whether miR-21-3p regulated ACACA and ACACB expression. We observed a decrease in both ACACA (1.6-fold) and ACACB (1.8-fold) expression by transfecting the miR-21-3p mimic into the 3 sample PHHs for 48 h (FIG. 9B). In addition, after transfecting of 100 nM of miR-21-3p hairpin inhibitor or negative-control inhibitor into HepG2 cells 24 h, the HepG2 cells were stimulated by the time course of berberine treatment for up to 8 h. Since the miR-21-3p induced by berberine was inhibited by the inhibitor, the mRNA expression levels of ACACA and ACACB are not decreased. This demonstrates that berberine induces miR-21-3p to reduce the mRNA expression levels of ACACA and ACACB (FIG. 9C). Transfection of the miR-21-3p mimic of the present invention into the HepG2 cells resulted in a 44% and a 50% decrease in the mRNA expression of ACACA and ACACB, respectively, at 24 h (FIG. 9D), and resulted in a decrease in the protein expression of ACACA (2.3-fold) and ACACB (1.6-fold), respectively, at 72 h (FIG. 9E). Following the 72-h transfection of the miR-21-3p mimic of the present invention, the intracellular malonyl-CoA concentration exhibited a decrease in both HepG2 cells (1.6-fold) and PHH cells (2.2-fold) (FIG. 9F). These results indicate that the miR-21-3p mimic of the present invention reduces the expression of ACACA and ACACB, and decreased the concentration of intracellular malonyl-CoA.

As for DGAT2, the important enzyme for triacylglycerol biosynthesis, it was predicted as a putative target of miR-21-3p with a miRanda-mirSVR score of −0.2515. The changes in DGAT2 expression levels resulted from berberine treatment were not significant among the PHH cells (FIG. 9A). This was consistent with the microarray data. However, we observed a 1.5-fold decrease in mRNA expression levels of DGAT2 in PHH cells following transfection of the miR-21-3p mimic of the present invention for 48 h (FIG. 9B). When miR-21-3p over-expressed in the HepG2 cells, a 2.3-fold decrease in the mRNA level of DGAT2 was observed at 24 h (FIG. 9D), and a 3.3-fold decrease in the protein level of DGAT2 was observed at 72 h (FIG. 9E).

With the technology similar to that used in Example 6, we subsequently examined the relationship between miR-21-3p and the 3' UTRs of ACACA, ACACB, and DGAT2, and found that the miR-21-3p suppressed the expression of ACACA, but not though its 3' UTR sequence (data not shown). The mRNA stability assays showed that berberine induced miR-21-3p, and miR-21-3p reduced the half-life of ACACA mRNA. In addition, no seed pairing occurred between the seed region of miR-21-3p and 3' UTR of ACACB, and miR-21-3p suppressed the expression of ACACB (a 1.4-fold decrease) by binding the exon 23 of ACACB. However, miR-21-3p did suppress DGAT2 expression (a 1.4-fold decrease) by pairing with the 3' UTR sequence of DGAT2. These results indicate that the miR-21-3p decreased hepatic lipid droplet accumulation by reducing the expression of ACACA, ACACB and DGAT2 in different ways.

As for other berberine-associated lipid metabolic genes, the transfection of 50 nM of miR-21-3p mimic caused a decrease in MTOR and RPTOR expression at 24 h (1.4-fold and 1.6-fold decrease, respectively), and a decrease in MTOR, RPTOR and HLCS expression at 48 h (2.5-fold, 2.2-fold and 1.5-fold decrease, respectively) following transfection (50 nM). This helps to explain that the miR-21-3p mimic of the present invention improves lipid metabolism.

The miR-21-3p mimic of the present invention targets to the 3' UTRs of MAT2A and MAT2B and decreases their expression directly. Over-expression of miR-21-3p up-regulates intracellular SAM contents to inhibit cell growth and induce apoptosis in HepG2 cells. In addition, the miR-21-3p mimic of the present invention decreases hepatic lipid droplet accumulation by reducing the half-life of ACACA mRNA and binding the exon 23 of ACACB and the 3' UTR sequence of DGAT2. Therefore, our results show that miR-21-3p can be a tumor suppressor and therapeutics for fatty liver disease and it is potential for treating liver diseases.

REFERENCES

1. Mato J M, Corrales F J, Lu S C, Avila M A (2002) S-Adenosylmethionine: a control switch that regulates liver function. The FASEB journal 16: 15-26.
2. Mato J M, Lu S C (2007) Role of S-adenosyl-L-methionine in liver health and injury. Hepatology 45: 1306-1312.
3. Kotb M, Mudd S H, Mato J M, Geller A M, Kredich N M, et al. (1997) Consensus nomenclature for the mammalian methionine adenosyltransferase genes and gene products. Trends in genetics: TIG 13: 51.
4. Mato J M, Alvarez L, Ortiz P, Pajares M A (1997) S-adenosylmethionine synthesis: molecular mechanisms and clinical implications. Pharmacol Ther 73: 265-280.
5. LeGros H L Jr, Halim A B, Geller A M, Kotb M (2000) Cloning, expression, and functional characterization of the beta regulatory subunit of human methionine adenosyltransferase (MAT II). J Biol Chem 275: 2359-2366.
6. Cai J, Mao Z, Hwang J-J, Lu S C (1998) Differential expression of methionine adenosyltransferase genes influences the rate of growth of human hepatocellular carcinoma cells. Cancer research 58: 1444-1450.
7. Lu S C, Mato J M (2008) S-Adenosylmethionine in cell growth, apoptosis and liver cancer. Journal of gastroenterology and hepatology 23: S73-S77.
8. Frau M, Tomasi M L, Simile M M, Demartis M I, Salis F, et al. (2012) Role of transcriptional and posttranscriptional regulation of methionine adenosyltransferases in liver cancer progression. Hepatology 56: 165-175.
9. Huang Z-Z, Mao Z, Cai J, Lu S C (1998) Changes in methionine adenosyltransferase during liver regeneration in the rat. American Journal of Physiology-Gastrointestinal and Liver Physiology 275: G14-G21.
10. Huang Z Z, Mato J M, Kanel G, Lu S C (1999) Differential effect of thioacetamide on hepatic methionine adenosyltransferase expression in the rat. Hepatology 29: 1471-1478.
11. Pañeda C, Gorospe I, Herrera B, Nakamura T, Fabregat I, et al. (2002) Liver cell proliferation requires methionine adenosyltransferase 2A mRNA upregulation. Hepatology 35: 1381-1391.
12. Garcea R, Daino L, Pascale R, Simile M M, Puddu M, et al. (1989) Inhibition of promotion and persistent nodule growth by S-adenosyl-L-methionine in rat liver carcinogenesis: role of remodeling and apoptosis. Cancer research 49: 1850-1856.
13. Martínez-Chantar M L, Corrales F J, Martínez-Cruz A, García-Trevijano E R, Huang Z-Z, et al. (2002) Spontaneous oxidative stress and liver tumors in mice lacking methionine adenosyltransferase 1A. The FASEB journal 16: 1292-1294.

14. Yang H, Sadda M R, Li M, Zeng Y, Chen L, et al. (2004) S-adenosylmethionine and its metabolite induce apoptosis in HepG2 cells: Role of protein phosphatase 1 and Bcl-xS. Hepatology 40: 221-231.
15. Martinez-Chantar M L, García-Trevijano E R, Latasa M U, Martín-Duce A, Fortes P, et al. (2003) Methionine adenosyltransferase II beta subunit gene expression provides a proliferative advantage in human hepatoma.
16. Liu Q, Wu K, Zhu Y, He Y, Wu J, et al. (2007) Silencing MAT2A gene by RNA interference inhibited cell growth and induced apoptosis in human hepatoma cells. Hepatology Research 37: 376-388.
17. Wang Q, Liu Q Y, Liu Z S, Qian Q, Sun Q, et al. (2008) Inhibition of hepatocellular carcinoma MAT2A and MAT2beta gene expressions by single and dual small interfering RNA. J Exp din Cancer Res 27: 72.
18. Ramani K, Yang H, Xia M, Ara A I, Mato J M, et al. (2008) Leptin's mitogenic effect in human liver cancer cells requires induction of both methionine adenosyltransferase 2A and 2b. Hepatology 47: 521-531.
19. Wang Q, Liu Q-Y, Liu Z-S, Qian Q, Sun Q, et al. (2008) Lentivirus mediated shRNA interference targeting MAT2B induces growth-inhibition and apoptosis in hepatocellular carcinoma. World journal of gastroenterology: WJG 14: 4633.
20. Kim, K.-H. Regulation of mammalian acetyl-coenzyme A carboxylase. Annual review of nutrition 17, 77-99 (1997).
21. Abu-Elheiga, L. et al. The subcellular localization of acetyl-CoA carboxylase 2. Proc Natl Acad Sci USA 97, 1444-1449 (2000).
22. Cases, S. et al. Cloning of DGAT2, a second mammalian diacylglycerol acyltransferase, and related family members. Journal of Biological Chemistry 276, 38870-38876 (2001).
23. Yen, C.-L. E., Stone, S. J., Koliwad, S., Harris, C. & Farese, R. V. Thematic review series: glycerolipids. DGAT enzymes and triacylglycerol biosynthesis. Journal of lipid research 49, 2283-2301 (2008).
24. Amin A, Subbaiah T, Abbasi K (1969) Berberine sulfate: antimicrobial activity, bioassay, and mode of action. Canadian journal of microbiology 15: 1067-1076.
25. Kuo C-L, Chi C-W, Liu T-Y (2004) The anti-inflammatory potential of berberine in vitro and in vivo. Cancer letters 203: 127-137.
26. Lee Y S, Kim W S, Kim K H, Yoon M J, Cho H J, et al. (2006) Berberine, a natural plant product, activates AMP-activated protein kinase with beneficial metabolic effects in diabetic and insulin-resistant states. Diabetes 55: 2256-2264.
27. Sun Y, Xun K, Wang Y, Chen X (2009) A systematic review of the anticancer properties of berberine, a natural product from Chinese herbs. Anti-cancer drugs 20: 757-769.
28. Iizuka N, Miyamoto K, Okita K, Tangoku A, Hayashi H, et al. (2000) Inhibitory effect of Coptidis Rhizoma and berberine on the proliferation of human esophageal cancer cell lines. Cancer letters 148: 19-25.
29. Mantena S K, Sharma S D, Katiyar S K (2006) Berberine, a natural product, induces G1-phase cell cycle arrest and caspase-3-dependent apoptosis in human prostate carcinoma cells. Molecular cancer therapeutics 5: 296-308.
30. Peng P-L, Hsieh Y-S, Wang C-J, Hsu J-L, Chou F-P (2006) Inhibitory effect of berberine on the invasion of human lung cancer cells via decreased productions of urokinase-plasminogen activator and matrix metalloproteinase-2. Toxicology and applied pharmacology 214: 8-15.
31. Kim S, Choi J H, Kim J B, Nam S J, Yang J-H, et al. (2008) Berberine suppresses TNF-a-induced MMP-9 and cell invasion through inhibition of AP-1 activity in MDA-MB-231 human breast cancer cells. Molecules 13: 2975-2985.
32. Wang L, Cao H, Lu N, Liu L, Wang B, et al. (2013) Berberine Inhibits Proliferation and Down-Regulates Epidermal Growth Factor Receptor through Activation of Cbl in Colon Tumor Cells. PloS one 8: e56666.
33. Wang L, Liu L, Shi Y, Cao H, Chaturvedi R, et al. (2012) Berberine induces caspase-independent cell death in colon tumor cells through activation of apoptosis-inducing factor. PloS one 7: e36418.
34. Liu B, Wang G, Yang J, Pan X, Yang Z, et al. (2011) Berberine inhibits human hepatoma cell invasion without cytotoxicity in healthy hepatocytes. PloS one 6: e21416.
35. Auyeung K K-W, Ko J K-S (2009) *Coptis chinensis* inhibits hepatocellular carcinoma cell growth through nonsteroidal anti-inflammatory drug-activated gene activation. International journal of molecular medicine 24: 571-577.
36. Tang J, Feng Y, Tsao S, Wang N, Curtain R, et al. (2009) Berberine and Coptidis Rhizoma as novel antineoplastic. Journal of ethnopharmacology 126: 5-17.
37. Hwang J-M, Kuo H-C, Tseng T-H, Liu J-Y, Chu C-Y (2006) Berberine induces apoptosis through a mitochondria/caspases pathway in human hepatoma cells. Archives of toxicology 80: 62-73.
38. Wang N, Feng Y, Zhu M, Tsang C M, Man K, et al. (2010) Berberine induces autophagic cell death and mitochondrial apoptosis in liver cancer cells: the cellular mechanism. Journal of cellular biochemistry 111: 1426-1436.
39. Ma C, Tang K, Liu Q, Zhu R, Cao Z (2013) Calmodulin as a potential target by which berberine induce cell cycle arrest in human hepatoma Bel7402 cells. Chemical biology & drug design.
40. Ambros V (2004) The functions of animal microRNAs. Nature 431: 350-355.
41. Hwang H, Mendell J (2006) MicroRNAs in cell proliferation, cell death, and tumorigenesis. British journal of cancer 94: 776-780.
42. Jansson M D, Lund A H (2012) MicroRNA and cancer. Molecular oncology.
43. Iorio M V, Croce C M (2012) microRNA involvement in human cancer. Carcinogenesis 33: 1126-1133.
44. Guo H, Ingolia N T, Weissman J S, Bartel D P (2010) Mammalian microRNAs predominantly act to decrease target mRNA levels. Nature 466: 835-840.
45. Selbach M, Schwanhäusser B, Thierfelder N, Fang Z, Khanin R, et al. (2008) Widespread changes in protein synthesis induced by microRNAs. Nature 455: 58-63.
46. Winter J, Jung S, Keller S, Gregory R I, Diederichs S (2009) Many roads to maturity: microRNA biogenesis pathways and their regulation. Nature cell biology 11: 228-234.
47. Azuma-Mukai A, Oguri H, Mituyama T, Qian Z R, Asai K, et al. (2008) Characterization of endogenous human Argonautes and their miRNA partners in RNA silencing. Proceedings of the National Academy of Sciences 105: 7964-7969.
48. Okamura K, Phillips M D, Tyler D M, Duan H, Chou Y T, et al. (2008) The regulatory activity of microRNA* species has substantial influence on microRNA and 3' UTR evolution. Nature structural & molecular biology 15: 354-363.
49. Goff L A, Davila J, Swerdel M R, Moore J C, Cohen R I, et al. (2009) Ago2 immunoprecipitation identifies predicted microRNAs in human embryonic stem cells and neural precursors. PLoS One 4: e7192.
50. Guo L, Lu Z (2010) The fate of miRNA* strand through evolutionary analysis: implication for degradation as merely carrier strand or potential regulatory molecule? PLoS One 5: e11387.
51. Okamura K, Chung W-J, Lai E C (2008) The long and short of inverted repeat genes in animals: microRNAs, mirtrons and hairpin RNAs. Cell Cycle 7: 2840-2845.
52. Yang J-S, Phillips M D, Betel D, Mu P, Ventura A, et al. (2011) Widespread regulatory activity of vertebrate microRNA* species. Rna 17: 312-326.
53. Liu X Y, Zhang L, Zhang Y, Yang J M (2012) Roles of eEF-2 kinase in cancer. Chinese Medical Journal 125: 2908-2913.
54. Chang, X. et al. Berberine reduces methylation of the MTTP promoter and alleviates fatty liver induced by a high-fat diet in rats. Journal of lipid research 51, 2504-2515 (2010).
55. Zhou, J. Y. et al. Chronic effects of berberine on blood, liver glucolipid metabolism and liver PPARs expression in diabetic hyperlipidemic rats. Biological and Pharmaceutical Bulletin 31, 1169-1176 (2008).
56. Kong, W. et al. Berberine is a novel cholesterol-lowering drug working through a unique mechanism distinct from statins. Nature medicine 10, 1344-1351 (2004).
57. Lee, Y. S. et al. Berberine, a natural plant product, activates AMP-activated protein kinase with beneficial metabolic effects in diabetic and insulin-resistant states. Diabetes 55, 2256-2264 (2006).
58. Liu, Y., Zhang, L., Song, H. & Ji, G. Update on Berberine in Nonalcoholic Fatty Liver Disease. Evidence-Based Complementary and Alternative Medicine 2013 (2013).
59. Donato, M. T. et al. Cytometric analysis for drug-induced steatosis in HepG2 cells. Chemico-biological interactions 181, 417-423 (2009).
60. Hinson, E. R. & Cresswell, P. The antiviral protein, viperin, localizes to lipid droplets via its N-terminal amphipathic α-helix. Proceedings of the National Academy of Sciences 106, 20452-20457 (2009).
61. Okamoto, Y., Tanaka, S. & Haga, Y. Enhanced GLUT2 gene expression in an oleic acid-induced in vitro fatty liver model. Hepatology research 23, 138-144 (2002).

What is claimed is:

1. A method for decreasing the expression of acetyl-CoA carboxylase 1 or 2 (ACACA or ACACB), diglyceride acyltransferase 2 (DGAT2), or methionine adenosyltransferase 2A or 2B (MAT2A or MAT2B) in a subject having a fatty liver disease, comprising administering an effective amount of a microRNA mimic containing a single strand RNA molecule of hsa-miR-21-3p (SEQ ID NO:35) to said subject.

2. The method according to claim 1, wherein said microRNA mimic is chemically modified for not being degraded by RNase.

3. The method according to claim 1, wherein said microRNA mimic is delivered into target cells by transfection and/or conjugate delivery.

4. The method according to claim 3, wherein said microRNA mimic is delivered into target cells by conjugate delivery and transfection.

5. The method according to claim 3, wherein said conjugate delivery delivers said microRNA mimic into target cells by binding an aptamer or cholesterol with the microRNA mimic.

6. The method according to claim 3, wherein the transfection delivers said microRNA mimic into target cells by using liposome, exosome, nanoparticle or virus.

7. The method according to claim 6, wherein said nanoparticle comprises lipid nanoparticle or polymer nanoparticle.

8. The method according to claim 1, which is administered by injection.

9. The method according to claim 1, wherein said administering decreases the expression of acetyl-CoA carboxylase 1 and 2 (ACACA and ACACB) and diglyceride acyltransferase 2 (DGAT2).

10. The method according to claim 4, wherein said conjugate delivery delivers said microRNA mimic into target cells by binding an aptamer or cholesterol with the microRNA mimic.

11. The method according to claim 4, wherein the transfection delivers said microRNA mimic into target cells by using liposome, exosome, nanoparticle or virus.

12. The method according to claim 1, wherein said administering decreases the expression of methionine adenosyltransferase 2A and 2B (MAT2A and MAT2B).

* * * * *

SEQUENCE LISTING

<160> NUMBER OF SEQ ID NOS: 68

<210> SEQ ID NO 1
<211> LENGTH: 18
<212> TYPE: DNA
<213> ORGANISM: Artificial Sequence
<220> FEATURE:
<223> OTHER INFORMATION: primer

<400> SEQUENCE: 1
gccaagggct ttgacttc                                                 18

<210> SEQ ID NO 2
<211> LENGTH: 19
<212> TYPE: DNA
<213> ORGANISM: Artificial Sequence
<220> FEATURE:
<223> OTHER INFORMATION: primer

<400> SEQUENCE: 2
ctgtctcgtc ggtagcata                                                19

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
acaatctacc acctacagcc                                               20

<210> SEQ ID NO 4
<211> LENGTH: 18
<212> TYPE: DNA
<213> ORGANISM: Artificial Sequence
<220> FEATURE:
<223> OTHER INFORMATION: primer

<400> SEQUENCE: 4
ccaacgagca gcataagc                                                   18

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
tggtttcaga agagcaagac                                                 20

<210> SEQ ID NO 6
<211> LENGTH: 18
<212> TYPE: DNA
<213> ORGANISM: Artificial Sequence
<220> FEATURE:
<223> OTHER INFORMATION: primer

<400> SEQUENCE: 6
attcccagaa gcatccac                                                   18

<210> SEQ ID NO 7
<211> LENGTH: 18
<212> TYPE: DNA
<213> ORGANISM: Artificial Sequence
<220> FEATURE:
<223> OTHER INFORMATION: primer

<400> SEQUENCE: 7
gatgaggagc ctggagac                                                   18

<210> SEQ ID NO 8
<211> LENGTH: 19
<212> TYPE: DNA
<213> ORGANISM: Artificial Sequence
<220> FEATURE:
<223> OTHER INFORMATION: primer

<400> SEQUENCE: 8
agaaatgccc acacaatcg                                                  19

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
ggcaaactcc ttccacttca                                                 20

<210> SEQ ID NO 10
<211> LENGTH: 18
<212> TYPE: DNA
<213> ORGANISM: Artificial Sequence
<220> FEATURE:
<223> OTHER INFORMATION: primer

<400> SEQUENCE: 10
catcatccag ccattccc                                                   18

```
<210> SEQ ID NO 11
<211> LENGTH: 19
<212> TYPE: DNA
<213> ORGANISM: Artificial Sequence
<220> FEATURE:
<223> OTHER INFORMATION: primer

<400> SEQUENCE: 11
caggacatcg gtggaatca                                                19

<210> SEQ ID NO 12
<211> LENGTH: 18
<212> TYPE: DNA
<213> ORGANISM: Artificial Sequence
<220> FEATURE:
<223> OTHER INFORMATION: primer

<400> SEQUENCE: 12
cttctgtagg gctggcat                                                 18

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
gaagactggt tgagtgggat                                               20

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
tgtcacaggc aagttcacat                                               20

<210> SEQ ID NO 15
<211> LENGTH: 19
<212> TYPE: DNA
<213> ORGANISM: Artificial Sequence
<220> FEATURE:
<223> OTHER INFORMATION: primer

<400> SEQUENCE: 15
agtcagtcaa gtttgcgtc                                                19

<210> SEQ ID NO 16
<211> LENGTH: 19
<212> TYPE: DNA
<213> ORGANISM: Artificial Sequence
<220> FEATURE:
<223> OTHER INFORMATION: primer

<400> SEQUENCE: 16
gagtcggagc ccacataga                                                19

<210> SEQ ID NO 17
<211> LENGTH: 20
<212> TYPE: DNA
<213> ORGANISM: Artificial Sequence
<220> FEATURE:
<223> OTHER INFORMATION: primer
```

<400> SEQUENCE: 17
cgtccctacc ttcttcttcc                                              20

<210> SEQ ID NO 18
<211> LENGTH: 18
<212> TYPE: DNA
<213> ORGANISM: Artificial Sequence
<220> FEATURE:
<223> OTHER INFORMATION: primer

<400> SEQUENCE: 18
taccactgag gcttctgc                                                18

<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19
acttcccgct cagagttaga                                              20

<210> SEQ ID NO 20
<211> LENGTH: 18
<212> TYPE: DNA
<213> ORGANISM: Artificial Sequence
<220> FEATURE:
<223> OTHER INFORMATION: primer

<400> SEQUENCE: 20
cgagaacctc cagcctta                                                18

<210> SEQ ID NO 21
<211> LENGTH: 19
<212> TYPE: DNA
<213> ORGANISM: Artificial Sequence
<220> FEATURE:
<223> OTHER INFORMATION: primer

<400> SEQUENCE: 21
ctccgcaact taggatggg                                               19

<210> SEQ ID NO 22
<211> LENGTH: 20
<212> TYPE: DNA
<213> ORGANISM: Artificial Sequence
<220> FEATURE:
<223> OTHER INFORMATION: primer

<400> SEQUENCE: 22
ctctctctgt ctctctctcg                                              20

<210> SEQ ID NO 23
<211> LENGTH: 19
<212> TYPE: DNA
<213> ORGANISM: Artificial Sequence
<220> FEATURE:
<223> OTHER INFORMATION: primer

<400> SEQUENCE: 23
gcaagtctgt tggtgctat                                               19

```
<210> SEQ ID NO 24
<211> LENGTH: 18
<212> TYPE: DNA
<213> ORGANISM: Artificial Sequence
<220> FEATURE:
<223> OTHER INFORMATION: primer

<400> SEQUENCE: 24
ttatctgggt gtgccctg                                                 18

<210> SEQ ID NO 25
<211> LENGTH: 18
<212> TYPE: DNA
<213> ORGANISM: Artificial Sequence
<220> FEATURE:
<223> OTHER INFORMATION: primer

<400> SEQUENCE: 25
gtggtagccg aggaggaa                                                 18

<210> SEQ ID NO 26
<211> LENGTH: 18
<212> TYPE: DNA
<213> ORGANISM: Artificial Sequence
<220> FEATURE:
<223> OTHER INFORMATION: primer

<400> SEQUENCE: 26
ggtcagagtc acgctgtc                                                 18

<210> SEQ ID NO 27
<211> LENGTH: 20
<212> TYPE: DNA
<213> ORGANISM: Artificial Sequence
<220> FEATURE:
<223> OTHER INFORMATION: primer

<400> SEQUENCE: 27
taccttcctt ctctccctcg                                               20

<210> SEQ ID NO 28
<211> LENGTH: 18
<212> TYPE: DNA
<213> ORGANISM: Artificial Sequence
<220> FEATURE:
<223> OTHER INFORMATION: primer

<400> SEQUENCE: 28
gtggtgctga atgttggc                                                 18

<210> SEQ ID NO 29
<211> LENGTH: 19
<212> TYPE: DNA
<213> ORGANISM: Artificial Sequence
<220> FEATURE:
<223> OTHER INFORMATION: primer

<400> SEQUENCE: 29
tttgtgccac ggttatcat                                                19

<210> SEQ ID NO 30
<211> LENGTH: 20
<212> TYPE: DNA
<213> ORGANISM: Artificial Sequence
<220> FEATURE:
<223> OTHER INFORMATION: primer
```

```
<400> SEQUENCE: 30
ccaagtaata gccagactcg                                              20

<210> SEQ ID NO 31
<211> LENGTH: 18
<212> TYPE: DNA
<213> ORGANISM: Artificial Sequence
<220> FEATURE:
<223> OTHER INFORMATION: primer

<400> SEQUENCE: 31
gaagttccca ggcatacg                                                18

<210> SEQ ID NO 32
<211> LENGTH: 22
<212> TYPE: DNA
<213> ORGANISM: Artificial Sequence
<220> FEATURE:
<223> OTHER INFORMATION: primer

<400> SEQUENCE: 32
gaccacgatg atgatagcat tg                                           22

<210> SEQ ID NO 33
<211> LENGTH: 20
<212> TYPE: DNA
<213> ORGANISM: Artificial Sequence
<220> FEATURE:
<223> OTHER INFORMATION: primer

<400> SEQUENCE: 33
ggtatcgtgg aaggactcat                                              20

<210> SEQ ID NO 34
<211> LENGTH: 17
<212> TYPE: DNA
<213> ORGANISM: Artificial Sequence
<220> FEATURE:
<223> OTHER INFORMATION: primer

<400> SEQUENCE: 34
ccttgcccac agccttg                                                 17

<210> SEQ ID NO 35
<211> LENGTH: 21
<212> TYPE: RNA
<213> ORGANISM: Artificial Sequence
<220> FEATURE:
<223> OTHER INFORMATION: siRNA

<400> SEQUENCE: 35
caacaccagu cgaugggcug u                                            21

<210> SEQ ID NO 36
<211> LENGTH: 24
<212> TYPE: RNA
<213> ORGANISM: Artificial Sequence
<220> FEATURE:
<223> OTHER INFORMATION: siRNA

<400> SEQUENCE: 36
ucacaaccuc cuagaaagag uaga                                         24
```

<210> SEQ ID NO 37
<211> LENGTH: 30
<212> TYPE: DNA
<213> ORGANISM: Artificial Sequence
<220> FEATURE:
<223> OTHER INFORMATION: primer

<400> SEQUENCE: 37
ataactagtg tgttagcctt ttttccccag                              30

<210> SEQ ID NO 38
<211> LENGTH: 29
<212> TYPE: DNA
<213> ORGANISM: Artificial Sequence
<220> FEATURE:
<223> OTHER INFORMATION: primer

<400> SEQUENCE: 38
ataaagcttg cactttctgc ttagggcaa                               29

<210> SEQ ID NO 39
<211> LENGTH: 32
<212> TYPE: DNA
<213> ORGANISM: Artificial Sequence
<220> FEATURE:
<223> OTHER INFORMATION: primer

<400> SEQUENCE: 39
ataacgcgtt ggcacttttt aagaacaaa gg                            32

<210> SEQ ID NO 40
<211> LENGTH: 34
<212> TYPE: DNA
<213> ORGANISM: Artificial Sequence
<220> FEATURE:
<223> OTHER INFORMATION: primer

<400> SEQUENCE: 40
ataaagctta aaattaaag caacaaaaga acaa                          34

<210> SEQ ID NO 41
<211> LENGTH: 39
<212> TYPE: DNA
<213> ORGANISM: Artificial Sequence
<220> FEATURE:
<223> OTHER INFORMATION: primer

<400> SEQUENCE: 41
cagctctgcc ctcccttctg ttgatatcag ccagacccc                    39

<210> SEQ ID NO 42
<211> LENGTH: 58
<212> TYPE: DNA
<213> ORGANISM: Artificial Sequence
<220> FEATURE:
<223> OTHER INFORMATION: primer

<400> SEQUENCE: 42
cactaaattc attataatgg tgaacaagat atctagggac agaatagcaa gcccaact    58

<210> SEQ ID NO 43
<211> LENGTH: 68
<212> TYPE: DNA
<213> ORGANISM: Artificial Sequence
<220> FEATURE:
<223> OTHER INFORMATION: primer

```
<400> SEQUENCE: 43
tttgatctga gctcaggcaa agcaaataat ggatatcaat gattttata ctatttcaca      60 caatttaa                                                              68

<210> SEQ ID NO 44
<211> LENGTH: 6
<212> TYPE: RNA
<213> ORGANISM: Artificial Sequence
<220> FEATURE:
<223> OTHER INFORMATION: seed region of siRNA

<400> SEQUENCE: 44 accacc                                                                6

<210> SEQ ID NO 45
<211> LENGTH: 80
<212> TYPE: DNA
<213> ORGANISM: Homo sapiens

<400> SEQUENCE: 45
ccttgtcggg tagcttatca gactgatgtt gactgttgaa tctcatggca acaccagtcg      60
atgggctgtc tgacattttg                                                 80

<210> SEQ ID NO 46
<211> LENGTH: 80
<212> TYPE: DNA
<213> ORGANISM: Pan troglodytes

<400> SEQUENCE: 46
ccttgtcggg tagcttatca gactgatgtt gactgttgaa tctcatggca acaccagtcg      60
atgggctgtc tgacattttg                                                 80

<210> SEQ ID NO 47
<211> LENGTH: 80
<212> TYPE: DNA
<213> ORGANISM: Macaca mulatta

<400> SEQUENCE: 47
ccttgtcggg tagcttatca gactgatgtt gactgttgaa tctcatggca acaccagtcg      60
atgggctgtc tgacattttg                                                 80

<210> SEQ ID NO 48
<211> LENGTH: 80
<212> TYPE: DNA
<213> ORGANISM: Otolemur crassicaudatus

<400> SEQUENCE: 48
ccttgtcggg tagcttatca gactgatgtt gactgttgaa tctcatggca acagcagtcg      60
atgggctgtc tgacattttg                                                 80

<210> SEQ ID NO 49
<211> LENGTH: 80
<212> TYPE: DNA
<213> ORGANISM: Tupaia chinensis

<400> SEQUENCE: 49
ccttgtcggg tagcttatca gactgatgtt gactgttgaa tctcatggca acagcagtcg      60
atgggctgtc tgacattttg                                                 80
```

```
<210> SEQ ID NO 50
<211> LENGTH: 80
<212> TYPE: DNA
<213> ORGANISM: Felis catus

<400> SEQUENCE: 50
ccttgtcggg tagcttatca gactgatgtt gactgttgaa tctcatggca acagcagtcg     60
atgggctgtc tgacattctg                                                 80

<210> SEQ ID NO 51
<211> LENGTH: 80
<212> TYPE: DNA
<213> ORGANISM: Bos taurus

<400> SEQUENCE: 51
ccttgtcggg tagcttatca gactgatgtt gactgttgaa tctcatggca acagcagtcg     60
atgggctgtc tgacattttg                                                 80

<210> SEQ ID NO 52
<211> LENGTH: 80
<212> TYPE: DNA
<213> ORGANISM: Canis lupus

<400> SEQUENCE: 52
ccttgtcggg tagcttatca gactgatgtt gactgttgaa tctcatggca acagcagtcg     60
atgggctgtc tgacattttg                                                 80

<210> SEQ ID NO 53
<211> LENGTH: 80
<212> TYPE: DNA
<213> ORGANISM: Loxodonta africana

<400> SEQUENCE: 53
tcttgtcggg tagcttatca gactgatgtt gactgttgaa tctcatggca acagcagtcg     60
atgggctgtc tgacattttg                                                 80

<210> SEQ ID NO 54
<211> LENGTH: 80
<212> TYPE: DNA
<213> ORGANISM: Cavia porcellus

<400> SEQUENCE: 54
ccttgtcggg tagcttatca gactgatgtt gactgttgaa tctcatggca acagcagtcg     60
atgggctgtc tgacattctg                                                 80

<210> SEQ ID NO 55
<211> LENGTH: 80
<212> TYPE: DNA
<213> ORGANISM: Erinaceus europaeus

<400> SEQUENCE: 55
ccttgtcggg tagcttatca gactgatgtt gcctgttgaa tctcatggca acagcagtcg     60
atgggctgtc tgactttttg                                                 80

<210> SEQ ID NO 56
<211> LENGTH: 80
<212> TYPE: DNA
<213> ORGANISM: Equus caballus
```

```
<400> SEQUENCE: 56
ccttgtcggg tagcttatca gactgatgtt gactgttgaa tctcatggca acagcagtcg    60
atgggctgtc tgacattttg                                                80

<210> SEQ ID NO 57
<211> LENGTH: 80
<212> TYPE: DNA
<213> ORGANISM: Mus musculus

<400> SEQUENCE: 57
ccttgtcgga tagcttatca gactgatgtt gactgttgaa tctcatggca acagcagtcg    60
atgggctgtc tgacattttg                                                80

<210> SEQ ID NO 58
<211> LENGTH: 80
<212> TYPE: DNA
<213> ORGANISM: Oryctolagus cuniculus

<400> SEQUENCE: 58
ctttgtcgga tagcttatca gactgatgtt gactgttgaa tctcatggca acagcagtcg    60
atgggctgtc tgacattttg                                                80

<210> SEQ ID NO 59
<211> LENGTH: 80
<212> TYPE: DNA
<213> ORGANISM: Rattus norvegicus

<400> SEQUENCE: 59
ccttgtcggg tagcttatca gactgatgtt gactgttgaa tctcatggca acagcagtcg    60
atgggctgtc tgacattttg                                                80

<210> SEQ ID NO 60
<211> LENGTH: 80
<212> TYPE: DNA
<213> ORGANISM: Sorex araneus

<400> SEQUENCE: 60
tcttgtcagg tagcttatca gattgatgtt gactgttgaa tctcatggca acagcagtcg    60
atgggctgtc tgacattttg                                                80

<210> SEQ ID NO 61
<211> LENGTH: 80
<212> TYPE: DNA
<213> ORGANISM: Monodelphis domestica

<400> SEQUENCE: 61
tcctgtcgga tagcttatca gactgatgtt gactgttgga tctcatggca acagcagtcg    60
atgagctgtc tgacattttg                                                80

<210> SEQ ID NO 62
<211> LENGTH: 80
<212> TYPE: DNA
<213> ORGANISM: Ornithorhynchus anatinus

<400> SEQUENCE: 62
tcctatcgga tagcttatca gactgatgtt gactgttaga tctcctggca acagcagtcg    60
atgggctgtc tgacattttg                                                80
```

```
<210> SEQ ID NO 63
<211> LENGTH: 21
<212> TYPE: RNA
<213> ORGANISM: Artificial Sequence
<220> FEATURE:
<223> OTHER INFORMATION: MAT2A-3' UTR-WT +180-200

<400> SEQUENCE: 63
cuauucuguc ccuaggcguuu u                                              21

<210> SEQ ID NO 64
<211> LENGTH: 21
<212> TYPE: RNA
<213> ORGANISM: Artificial Sequence
<220> FEATURE:
<223> OTHER INFORMATION: MAT2A-3' UTR-mutant +180-200

<400> SEQUENCE: 64
cuauucuguc ccuagauauc u                                               21

<210> SEQ ID NO 65
<211> LENGTH: 22
<212> TYPE: RNA
<213> ORGANISM: Artificial Sequence
<220> FEATURE:
<223> OTHER INFORMATION: MAT2A-3' UTR-WT +1267-1288

<400> SEQUENCE: 65
acaggggguc uggcuggugu ua                                              22

<210> SEQ ID NO 66
<211> LENGTH: 22
<212> TYPE: RNA
<213> ORGANISM: Artificial Sequence
<220> FEATURE:
<223> OTHER INFORMATION: MAT2A-3' UTR-mutant +1267-1288

<400> SEQUENCE: 66
acaggggguc uggcugauau ca                                              22

<210> SEQ ID NO 67
<211> LENGTH: 20
<212> TYPE: RNA
<213> ORGANISM: Artificial Sequence
<220> FEATURE:
<223> OTHER INFORMATION: MAT2B-3' UTR-WT +399-418

<400> SEQUENCE: 67
uauaaaaauc auugguguuc                                                 20

<210> SEQ ID NO 68
<211> LENGTH: 20
<212> TYPE: RNA
<213> ORGANISM: Artificial Sequence
<220> FEATURE:
<223> OTHER INFORMATION: MAT2B-3' UTR-mutant +399-418

<400> SEQUENCE: 68
uauaaaaauc auugauaucu                                                 20
```